United States Patent
Hwang et al.

(10) Patent No.: US 9,863,915 B2
(45) Date of Patent: Jan. 9, 2018

(54) FLEXIBLE DEVICE AND BENDING DETECTION APPARATUS THEREFOR

(71) Applicant: LG Display Co., Ltd., Seoul (KR)

(72) Inventors: Heeseo Hwang, Jeollabuk-do (KR); HaZoong Kim, Gyeonggi-do (KR); SungWan Hong, Seoul (KR)

(73) Assignee: LG Display Co., Ltd., Seoul (KR)

( * ) Notice: Subject to any disclaimer, the term of this patent is extended or adjusted under 35 U.S.C. 154(b) by 473 days.

(21) Appl. No.: 14/468,568

(22) Filed: Aug. 26, 2014

(65) Prior Publication Data
US 2015/0090044 A1  Apr. 2, 2015

(30) Foreign Application Priority Data

Oct. 1, 2013  (KR) .................. 10-2013-0117187

(51) Int. Cl.
| | | |
|---|---|---|
| *G01N 27/72* | (2006.01) | |
| *G01N 3/20* | (2006.01) | |
| *G01L 1/12* | (2006.01) | |
| *G06F 1/16* | (2006.01) | |
| *G06F 3/01* | (2006.01) | |

(52) U.S. Cl.
CPC ............. *G01N 27/72* (2013.01); *G01L 1/127* (2013.01); *G01N 3/20* (2013.01); *G06F 1/1652* (2013.01); *G06F 3/017* (2013.01); *G06F 2203/04102* (2013.01)

(58) Field of Classification Search
CPC  G01L 1/127; G01L 1/14; G01L 9/007; G01N 27/72; G01N 33/0031; G01N 3/20; G06F 1/1652; G06F 2203/04102; G06F 3/017
See application file for complete search history.

(56) References Cited

U.S. PATENT DOCUMENTS

| | | | | |
|---|---|---|---|---|
| 7,498,802 B2 * | 3/2009 | Takahata | .............. | G01D 5/2066 324/207.15 |
| 8,701,469 B2 * | 4/2014 | Ober | .................. | G01N 33/0031 73/61.41 |
| 9,038,483 B2 * | 5/2015 | Nagarajan | ................ | G01B 7/16 324/207.15 |

(Continued)

FOREIGN PATENT DOCUMENTS

| | | |
|---|---|---|
| CN | 101164088 A | 4/2008 |
| CN | 101490565 A | 7/2009 |

(Continued)

OTHER PUBLICATIONS

Communication dated Feb. 11, 2015 from the European Patent Office in counterpart European Application No. 14187357.0.

(Continued)

*Primary Examiner* — Freddie Kirkland, III
(74) *Attorney, Agent, or Firm* — Morgan, Lewis & Bockius LLP

(57) ABSTRACT

A bending detection apparatus for a flexible device includes a plurality of antennas disposed to be bent together with a flexible device; and a bending detection unit for detecting bending of the flexible device based on inductances of the plurality of antennas or information corresponding to the inductances, a bending detection method for a flexible device, and a flexible device.

21 Claims, 18 Drawing Sheets

(56) References Cited

U.S. PATENT DOCUMENTS

| | | | | |
|---|---|---|---|---|
| 2005/0146423 A1* | 7/2005 | Hattori | ............... | B60C 19/00 |
| | | | | 340/438 |
| 2006/0254369 A1* | 11/2006 | Yoon | ............... | A61B 5/6804 |
| | | | | 73/862.041 |
| 2008/0007253 A1* | 1/2008 | Takahata | ............ | G01D 5/2066 |
| | | | | 324/207.22 |
| 2008/0010110 A1 | 1/2008 | Neuhauser et al. | | |
| 2013/0131554 A1* | 5/2013 | Dunias | ............ | A61B 5/1071 |
| | | | | 600/595 |
| 2013/0241795 A1* | 9/2013 | Sung | ............ | H01Q 1/50 |
| | | | | 343/861 |

FOREIGN PATENT DOCUMENTS

| | | |
|---|---|---|
| CN | 102753094 A | 10/2012 |
| CN | 103326105 A | 9/2013 |
| EP | 2 353 505 A1 | 8/2011 |
| JP | 2003-057003 A | 2/2003 |
| JP | 2004-069358 A | 3/2004 |
| JP | 2011-089923 A | 5/2011 |
| JP | 2013-105312 A | 5/2013 |
| JP | 2013-518660 A | 5/2013 |
| WO | 2009/072042 A2 | 6/2009 |
| WO | 2009072042 A2 | 6/2009 |

OTHER PUBLICATIONS

S. Wattanasarn, et al., 3D Flexible Tactile Sensor Using Electromagnetic Induction Coils, The Univerisity of Tokyo, Japan, 2012 IEEE 25th International Conference on Micro Electro Mechanical Systems (MEMS), Paris, France, Jan. 29-Feb. 2, 2012, pp. 488-491.
R. Wijesiriwardana, Inductive Fiber-Meshed Strain and Displacement Transducers for Respiratory Measuring Systems and Motion Capturing Systems, IEEE Sensors Journal, vol. 6, No. 3, Jun. 2006, pp. 571-579.
Office Action dated Aug. 2, 2016, issued in corresponding Chinese Patent Application No. 201410494435.6.
Office Action dated Aug. 4, 2016, issued in corresponding Japanese Patent Application No. 2014-188632.

* cited by examiner

FLEXIBLE DEVICE AND BENDING DETECTION APPARATUS THEREFOR

CROSS-REFERENCE TO RELATED APPLICATION

This application claims the benefit Korean Patent Application No. 10-2013-0117187, filed in Korea on Oct. 1, 2013, which is hereby incorporated by reference for all purposes as if fully set forth herein.

BACKGROUND OF THE INVENTION

Field of the Invention

The present invention relates to a flexible device and a bending detection apparatus therefore.

Description of the Related Art

Recently developed flexible devices refer to devices that can be deflected, bent, or rolled without being significantly damaged and are made using a thin and flexible substrate which is different from flat panel displays.

The flexible devices may be used in mobile technology as well as in general TVs, and may be used in various application fields such as electronic newspapers, electronic books, TVs, computers, PDAs, vehicle related displays, and wrist wearable displays, including existing flat panel displays as they can be manufactured using clothes or fibers.

Display characteristics of the flexible devices may be changed according to bending characteristics, and various functions may be controlled or performed using these bending characteristics.

Accordingly, a technology for detecting a bending state of a flexible device is required.

SUMMARY OF THE INVENTION

Accordingly, the present invention is directed to a flexible device and a bending detection apparatus therefor that substantially obviates one or more of the problems due to limitations and disadvantages of the related art.

An object of the present invention is to provide a flexible device, and a method and an apparatus for detecting the bending thereof.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purposed of the present invention, as embodied and broadly described, a bending detection apparatus includes a plurality of antennas disposed to be bent together with a flexible device; and a bending detection unit for detecting bending of the flexible device based on inductances of the plurality of antennas or information corresponding to the inductances.

In aspect, a bending detection method for a flexible device includes measuring inductances of a plurality of antennas disposed to be bent together with the flexible device or information corresponding to the inductances; and detecting bending of the flexible device based on the measurement result.

In another aspect, a bending detection apparatus for a flexible device includes a generator for supplying a current or a voltage to at least one of the plurality of antennas disposed to be bent together with the flexible device; a measurement unit for measuring a voltage or an inductance of the antenna to which the current or the voltage is supplied or another antenna; and a controller for detecting bending of the flexible device based on the measurement result of the measurement unit.

In another aspect, a flexible device includes a plurality of antennas disposed to be bent together with the flexible device and to which a voltage or a current is applied for detection of bending of the flexible device, and the plurality of antennas are disposed at different locations.

In another aspect, a flexible device includes: a flexible panel; an antenna unit including a plurality of antennas disposed to be bent together with the flexible panel; and a bending detection unit for detecting bending of the flexible device based on inductances of the plurality of antennas or information corresponding to the inductances.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE EMBODIMENTS

Figure 1:
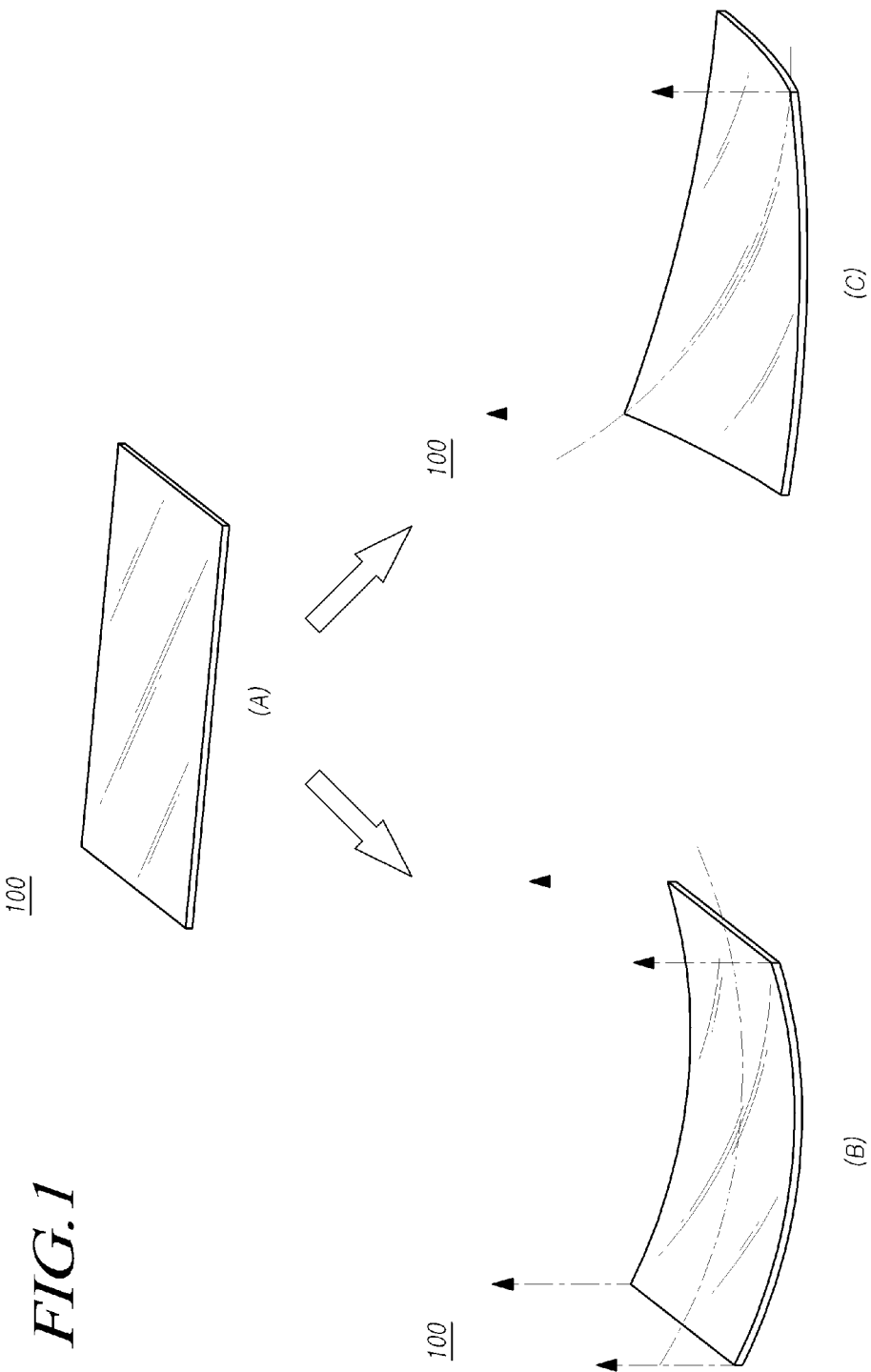
FIG. 1 is a view exemplifying bending of a flexible device.

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected", "coupled" or "joined" to another component, a third component may be "interposed" between the first and second components, although the first component may be directly "connected", "coupled" or "joined" to the second component.

FIG. 1 is a view exemplifying bending of a flexible device 100.

With reference to FIG. 1, a flexible device refers to a device that can be deflected, bent, twisted or rolled without being significantly damaged and is made using a thin and flexible substrate which is different from a general flat panel display.

The flexible device 100 may be used in mobile technology as well as general TVs, and may be used in various application fields such as electronic newspapers, electronic books, TVs, computers, PDAs, vehicle related displays, and wrist wearable displays, including existing flat panel displays as they can be manufactured using clothes or fibers.

Meanwhile, the flexible device 100 according to the embodiment of the present invention has varying display characteristics due to the bending characteristics by which it can be deflected, bent, or rolled, and can control or perform a process for various functions by using these bending characteristics.

For example, a process of enlarging or reducing a screen output on a screen may be performed or a process related to the processing of a screen, for example, of turning to the next page may be performed when it is bent in one direction.

Accordingly, a method and an apparatus for efficiently and accurately detecting bending of a flexible device 100 according to an embodiment of the present invention are suggested here.

The bending of the flexible device 100 according to the embodiment of the present invention refers to all states in which a flat device is deformed so as not to be flat as in FIG. 1A, and may be largely classified into a first bending type in which the flexible device 100 is transversely or longitudinally bent or partially bent as in FIG. 1B and a second bending type in which the flexible device 100 is twisted as in FIG. 1C.

In the flexible device 100 according to the embodiment of the present invention, a bending direction, a bending location, a bending strength, and the like of the flexible device 100 may be detected based on inductances of a plurality of antennas that may be bent together with the flexible device 100 or voltages through which inductances of the antennas may be calculated.

Hereinafter, a flexible device 100, and a method and an apparatus for detecting bending of the flexible device 100 according to exemplary embodiments of the present invention will be described in more detail.

Figure 2:
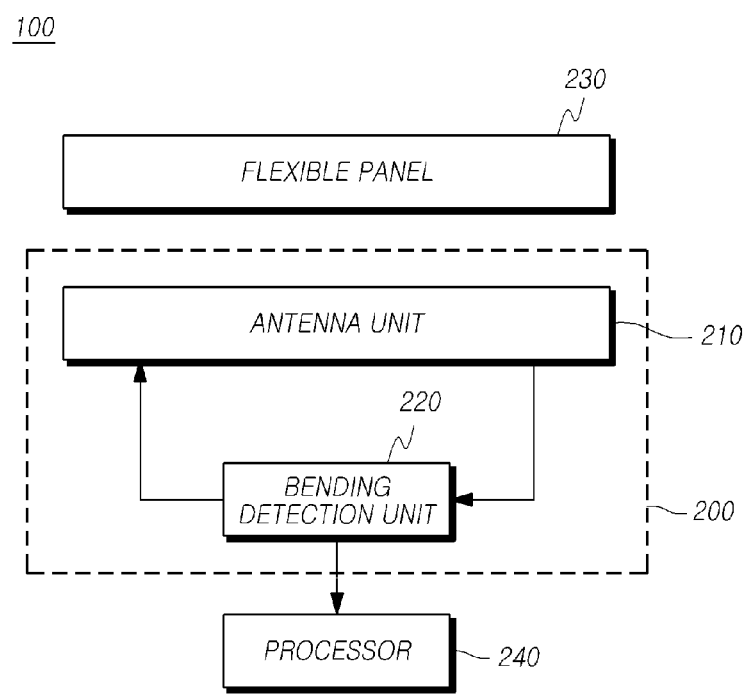
FIG. 2 is a schematic block diagram of a flexible device according to an embodiment of the present invention.

FIG. 2 is a schematic block diagram of a flexible device 100 according to an embodiment of the present invention.

With reference to FIG. 2, the flexible device 100 includes a bending detection apparatus 200 for detecting bending of the flexible device 100, and a flexible panel 230 including a flexible substrate in which a switching element is formed.

With reference to FIG. 2, the bending detection apparatus 200 includes an antenna unit 210 including a plurality of antennas disposed to be bent together with the flexible device 100; and a bending detection unit 220 for detecting bending of the flexible device 100 based on inductances for the plurality of antennas or information (for example, a voltage or a current) corresponding to the inductances.

The plurality of antennas included in the antenna unit 210 may generate inductances as a voltage or a current is applied to the flexible device 100 for detecting bending of the flexible device 100.

Meanwhile, as shown in FIG. 2, the flexible device 100 according to the present invention may further include a processor 240 for controlling or performing a process corresponding to a bending detection result of the flexible device 100.

Here, the process corresponding to the bending detection result may be, for example, one of a process for enlarging or reducing a screen and a process for converting a screen, such as turning a page and turning an image, and may be any process that can be performed by using a bending detection result as input information, without being limited thereto.

As described above, bending of the flexible device 100 may be detected based on inductances for a plurality of antennas or information such as a voltage or a current corresponding to the inductances.

The bending detection unit 220 of the flexible device 100 will be described in more detail with reference to FIG. 3 to describe a bending detection method.

The flexible device 100 shown in FIG. 2 may be, for example, a general TV and a computer such as a desktop monitor or a notebook, and may be a mobile terminal such as a smartphone, a tablet, or a PDA. In addition, the flexible device 100 may be an electronic device in various application fields such as a smart watch, a wearable device, an electronic book, an electronic newspaper, and a vehicle related display. In a narrower sense, the flexible device 100 may be a flexible display included in the above-described devices.

Figure 3:
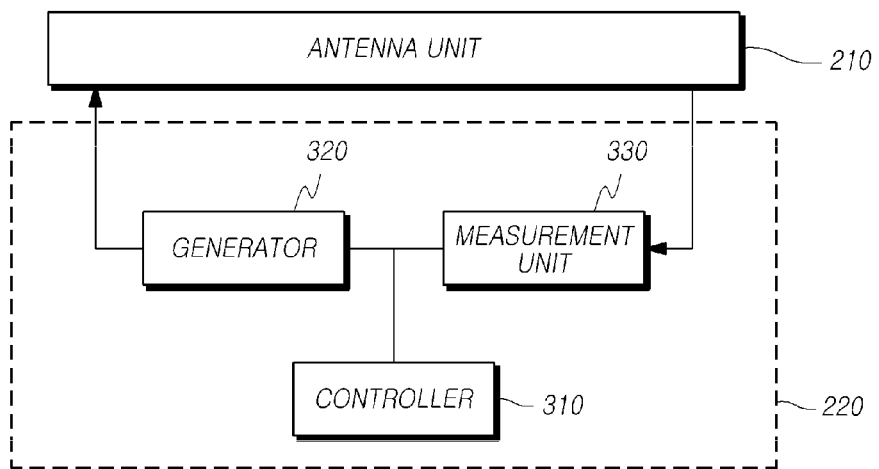
FIG. 3 is a schematic block diagram of a bending detection apparatus for a flexible device according to an embodiment of the present invention.

FIG. 3 is a schematic block diagram of a bending detection apparatus 200 for a flexible device 100 according to an embodiment of the present invention.

With reference to FIG. 3, the bending detection unit 220 included in the bending detection unit 200 of the flexible device 100 includes a controller 310 for performing an overall control function for detecting bending, a generator 320 for generating a signal for detecting bending, and a measurement unit 330 for measuring inductances for detecting bending or information (for example, a voltage or a current) related to the inductances.

The generator 320 supplies a current or a voltage as a signal for detecting bending to at least one of the plurality of antennas included in the antenna unit 210 and disposed to be bent together with the flexible device 100.

The measurement unit 330 measures a voltage or an inductance of the antenna to which a current or a voltage is supplied by the generator 320, or another antenna.

The controller 310 detects bending of the flexible device 100 based on the measurement result of the measurement unit 330. Here, the detection of bending includes a bending location, a bending direction, and a bending strength of the flexible device 100.

The plurality of antennas included in the antenna unit 210 in the bending detection apparatus 200 may be disposed in a suitable structure for generating and measuring inductances.

For example, the plurality of antennas may be disposed at different locations such that different inductances may be generated due to bending of the flexible device 100.

As an example, the plurality of antennas may be disposed such that disposition angles of the antennas are different.

In another example, the plurality of antennas may be disposed such that the antennas are symmetrical with respect to a vertical line or a horizontal line.

Meanwhile, a predetermined number of antennas designed according to a predefined degree of bending detection accuracy may be disposed.

For example, the antennas may be designed such that the number of antennas increases as a higher degree of bending detection accuracy is defined and the number of antennas decreases as a lower degree of bending detection accuracy is defined.

Meanwhile, if the number of antennas increases, a circuit and a procedure for measuring inductances may be more complex and a larger amount of calculations may be necessary. Thus, the number of antennas and the disposition pattern of the antennas need to be designed in consideration of the bending detection accuracy, circuit complexity, and the amount of calculations.

Meanwhile, the bending detection method of the flexible device 100 according to the embodiment of the present invention is based on a change in inductance, and may be largely classified into a method of detecting bending of the flexible device 100 based on a self-inductance (Ls), and a method of detecting bending of the flexible device based on a mutual inductance (Lm) according to the type of the inductance.

Here, an inductance is a quantity that represents a ratio of electromotive forces generated by electromagnetic induction due to a change in current flowing through a circuit included in an antenna, and may be classified into a self-inductance (Ls) and a mutual inductance (Lm) according to the cause of the change in magnetic flux. According to an induced electromotive force (a counter electromotive force), that is, the cause of a change in magnetic flux passing through a circuit, an inductance generated when a counter electromotive force is induced by a change in a current flowing through the circuit on its own is referred to as "a self-inductance (Ls)", and an inductance induced by a change in a current flowing through a circuit coupled with a counterpart is referred to as "a mutual inductance (Lm)".

When bending is detected based on a self-inductance, the bending detection unit 220 detects bending of the flexible device 100 based on the self-inductances (Ls) of the plurality of antennas.

When bending is detected based on a mutual inductance, the bending detection unit 220 detects bending of the flexible device 100 based on mutual inductances (Lm) in two or more pairs of antennas including a combination of a first antenna and a second antenna selected from the plurality of antennas.

As described above, the bending detection method of the flexible device 100 may be one of a bending detection method based on a self-inductance and a bending detection method based on a mutual inductance, and a disposition pattern of antennas may be changed according to the type of the bending detection method, that is, according to the type of inductance.

Hereinafter, the bending detection method based on self-inductance (Ls) and an antenna disposition pattern in the method will be described in more detail with reference to FIGS. 4 to 10, and the bending detection method based on a mutual inductance (Lm) and an antenna disposition pattern in the method will be described in more detail with reference to FIGS. 11 to 17.

Figure 4:
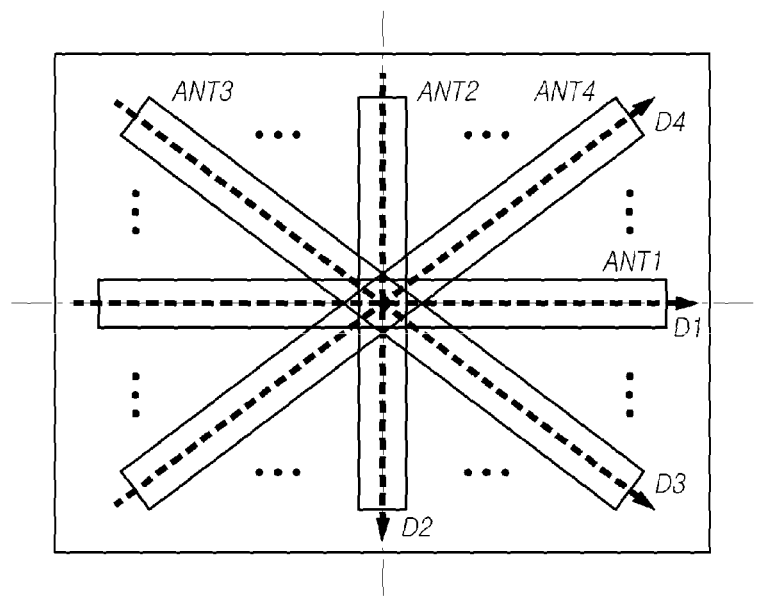
FIG. 4 is an exemplary view of the disposition of antennas when bending of the flexible device 100 according to the embodiment of the present invention is detected based on self-inductance.

FIG. 4 is an exemplary view of the disposition of antennas when bending of the flexible device 100 according to the embodiment of the present invention is detected based on self-inductance (Ls).

With reference to FIG. 4, when the bending detection unit 220 detects bending of the flexible device 100 based on self-inductances of a plurality of antennas, the plurality of antennas ANT1, ANT2, . . . included in the antenna unit 210 are disposed such that disposition directions D1, D2, . . . thereof are different from each other. Here, the number of the antennas may be two or more.

As an example of the antenna disposition pattern in which disposition directions of the antennas are different from each other, the plurality of antennas ANT1, ANT2, . . . may be disposed such that the disposition angles thereof with respect to the center of the flexible device 100 are different so that the disposition directions thereof are different.

When the plurality of antennas ANT1, ANT2, . . . are disposed such that the disposition directions D1, D2, . . . thereof are different from each other, the plurality of antennas ANT1, ANT2, . . . may be disposed such that opposite ends of at least one of the plurality of antennas ANT1, ANT2, . . . may be closer to each other than opposite ends of the remaining antennas after the flexible device 100 is bent.

According to the antenna disposition characteristics, if the flexible device 100 is bent in a specific direction, the plurality of antennas ANT1, ANT2, . . . also are bent. However, the bending degrees of the plurality of antennas ANT1, ANT2, . . . may be different according to the unique disposition directions thereof.

Accordingly, change values of the self-inductances measured in the plurality of antennas ANT1, ANT2, . . . may vary.

For example, the size of an internal area of an antenna disposed in a disposition direction most corresponding to the bending direction of the flexible device 100 through which a magnetic flux passes vary more than the sizes of internal areas of other antennas, and accordingly, a change in magnetic flux of an antenna disposed in a disposition direction most corresponding to the bending direction of the flexible device 100 becomes largest and a change value of the self-inductance Ls also changes the most.

That is, before and after the bending of the flexible device 100, a change value of the self-inductance measured in an antenna disposed in a disposition direction most corresponding to the bending direction of the flexible device 100 is the largest.

With reference to FIG. 4, the plurality of antennas ANT1, ANT2, . . . disposed in the above-described antenna disposition pattern may include, for example, two or more antennas of at least one loop antenna (for example, ANT1) disposed in a transverse direction of the flexible device 100, at least one loop antenna (for example, ANT2) disposed in a longitudinal direction of the flexible device 100, and at least one loop antenna (for example, ANT3 and ANT4) disposed in a diagonal direction of the flexible device 100, the two or more antennas having different disposition directions.

Meanwhile, with reference to FIG. 4, the plurality of antennas ANT1, ANT2, . . . may be two or more antennas, but may be designed to be three or more antennas according to a predefined bending detection accuracy.

Figure 5:
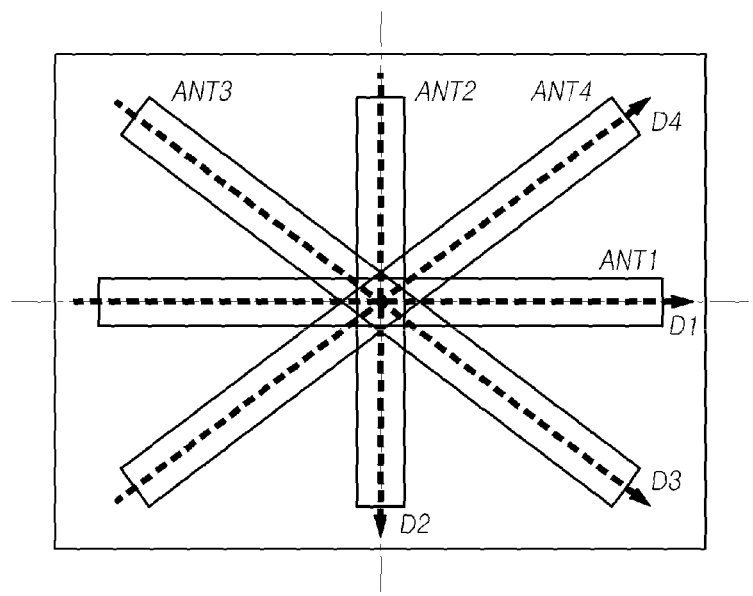
FIG. 5 is another exemplary view of the disposition of antennas when bending of the flexible device 100 according to the embodiment of the present invention is detected based on self-inductance.

FIG. 5 is another exemplary view of disposition of antennas when bending of the flexible device 100 according to the embodiment of the present invention is detected based on a self-inductance (Ls).

FIG. 5 is a view showing the antenna unit 210 when the number of antennas is four in FIG. 4, that is, the antenna unit 210 including four antennas ANT1, ANT2, ANT3, and ANT4.

With reference to FIG. 5, the antenna unit 210 includes one loop antenna ANT1 disposed in a transverse direction D1 of the flexible device 100, one loop antenna ANT2 disposed in a longitudinal direction D2 of the flexible device 100, and two loop antennas ANT3 and ANT4 disposed in two diagonal directions D3 and D4 of the flexible device 100.

Hereinafter, a method of detecting bending of the flexible device 100 which has the antenna disposition pattern shown in FIG. 5 will be described in more detail with reference to FIGS. 6 to 10.

Figure 6:
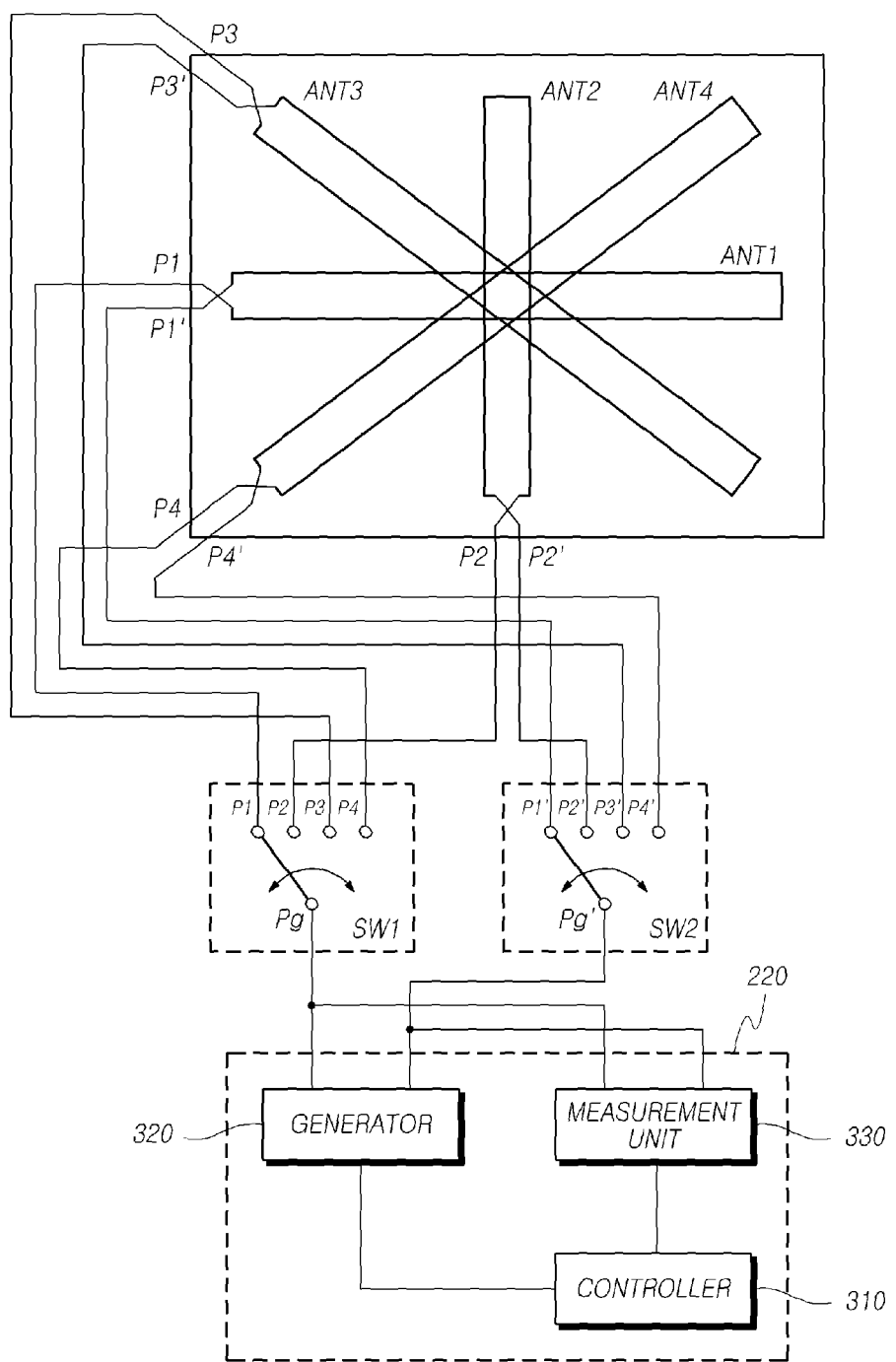
FIG. 6 is a view showing a connection structure of an antenna unit and a bending detection unit when bending of a flexible device is detected based on self-inductance according to an embodiment of the present invention.

FIG. 6 is a view showing a connection structure of the antenna unit 210 and the bending detection unit 220 when bending of the flexible device 100 according to the embodiment of the present invention is detected based on a self-inductance (Ls).

With reference to FIG. 6, each of the four antennas ANT1, ANT2, ANT3, and ANT4 include a first port P1, P2, P3, or P4 to which a voltage or a current may be supplied from the generator 320, and a second port P1', P2', P3', or P4' from which a voltage, a current, or a self-inductance (Ls) may be measured by a measurement unit 330.

With reference to FIG. 6, each of the four antennas ANT1, ANT2, ANT3, and ANT4 is switched by a first switch SW1 to receive a voltage or a current from the generator 320. That is, one of the first ports P1, P2, P3, and P4 of the four antennas ANT1, ANT2, ANT3, and ANT4 is selectively connected to a port Pg of the generator 320 to receive a voltage or a current from the generator 320.

With reference to FIG. 6, each of the four antennas ANT1, ANT2, ANT3, and ANT4 is switched by a second switch SW2 such that a voltage, a current, or a self-inductance Ls may be measured by the measurement unit 330. That is, one of the second ports P1', P2', P3', and P4' of the four antennas ANT1, ANT2, ANT3, and ANT4 is selectively connected to a port Pg' of the measurement unit 330 such that a voltage, a current, or a self-inductance (Ls) thereof may be measured by the measurement unit 330.

The antenna may be selected by controlling operations of the two switches SW1 and SW2 by the controller 310.

With reference to FIG. 6, for example, the controller 310 makes a control such that the first switch SW1 connects the port Pg of the generator 320 to a port P1 of the antenna ANT1 of the first ports P1, P2, P3, and P4 of the four antennas ANT1, ANT2, ANT3, and ANT4 and the second switch SW2 connects the port Pg' of the measurement unit 330 to a port P1' of the antenna ANT1 of the second ports P1', P2', P3', and P4' of the four antennas ANT1, ANT2, ANT3, and ANT4 such that the antenna ANT1 of the four antennas ANT1, ANT2, ANT3, and ANT4 is selected as an antenna which will receive a voltage or a current from the generator 320 and an antenna whose self-inductance or information (a voltage or a current) corresponding to the self-inductance. Then, the generator 320, the antenna ANT1, and the measurement unit 330 are connected in series.

After the antenna ANT1 is selected, the generator 320 supplies a voltage or a current to the selected antenna ANT1.

Accordingly, a current change is generated in a circuit including the antenna ANT1 to generate a self-inductance (Ls), and the measurement unit 330 measures a self-inductance generated by the antenna ANT1 or information corresponding to the inductance.

The controller 310 measures self-inductances generated by the antenna ANT1 before and after the flexible device 100 is bent, calculates a change value of the measured self-inductances, and records a change value of the calculated self-inductances.

The procedure of calculating and recording a change value of the self-inductances of the antenna ANT1 is performed in the same way for the antennas ANT2, ANT3, and ANT4.

Thereafter, after the self-inductances of the plurality of antennas ANT1, ANT2, ANT3, and ANT4 before and after the flexible device 100 is bent, the controller 310 of the bending detection unit 220 may recognize change values of the self-inductances of the plurality of antennas ANT1, ANT2, ANT3, and ANT4 measured before and after the flexible device 100 is bent, compares the recognized change values of the self-inductances of the plurality of antennas ANT1, ANT2, ANT3, and ANT4, and determines a bending direction of the flexible device 100 based on the comparison result and the disposition directions of the plurality of antennas ANT1, ANT2, ANT3, and ANT4.

For example, if the change value of the self-inductance of the antenna ANT1 disposed transversely before and after the flexible device 100 is bent is maximal, the transverse direction which is the disposition direction of the antenna ANT1 whose change value of self-inductance is maximal is the bending direction of the flexible device 100.

The controller 310 of the bending detection unit 220 may determine a bending strength of the flexible device 100 based on the magnitudes of the recognized change values of the self-inductances of the plurality of antennas ANT1, ANT2, ANT3, and ANT4.

Meanwhile, as the flexible device 100 is bent, opposite ends of an antenna of the plurality of antennas ANT1, ANT2, ANT3, and ANT4 disposed in a direction corresponding to the bending direction of the flexible device 100 become closer and the size of the internal area becomes smaller, so that a magnetic flux is changed and self-inductance decreases after the flexible device 100 is bent.

Accordingly, the antenna of the plurality of antennas ANT1, ANT2, ANT3, and ANT4 disposed in a direction most corresponding to the bending direction of the flexible device 100 has a maximum change value of self-inductance before and after the flexible device 100 is bent.

Hereinafter, self-inductances (Ls) measured in the antennas ANT1, ANT2, ANT3, and ANT4 while a degree (bending strength) by which the flexible device 100 is bent transversely is changed will be described with reference to FIG. 7, and an example of detecting bending of the flexible device 100 when the flexible device 100 is bent transversely by a specific degree will be described with reference to FIG. 8.

Further, self-inductances (Ls) measured in the antennas ANT1, ANT2, ANT3, and ANT4 while a degree (bending strength) by which the flexible device 100 is bent diagonally is changed and change values thereof will be described with reference to FIG. 9, and an example of detecting bending of the flexible device 100 when the flexible device 100 is bent diagonally by a specific degree will be described with reference to FIG. 10.

Figure 7:
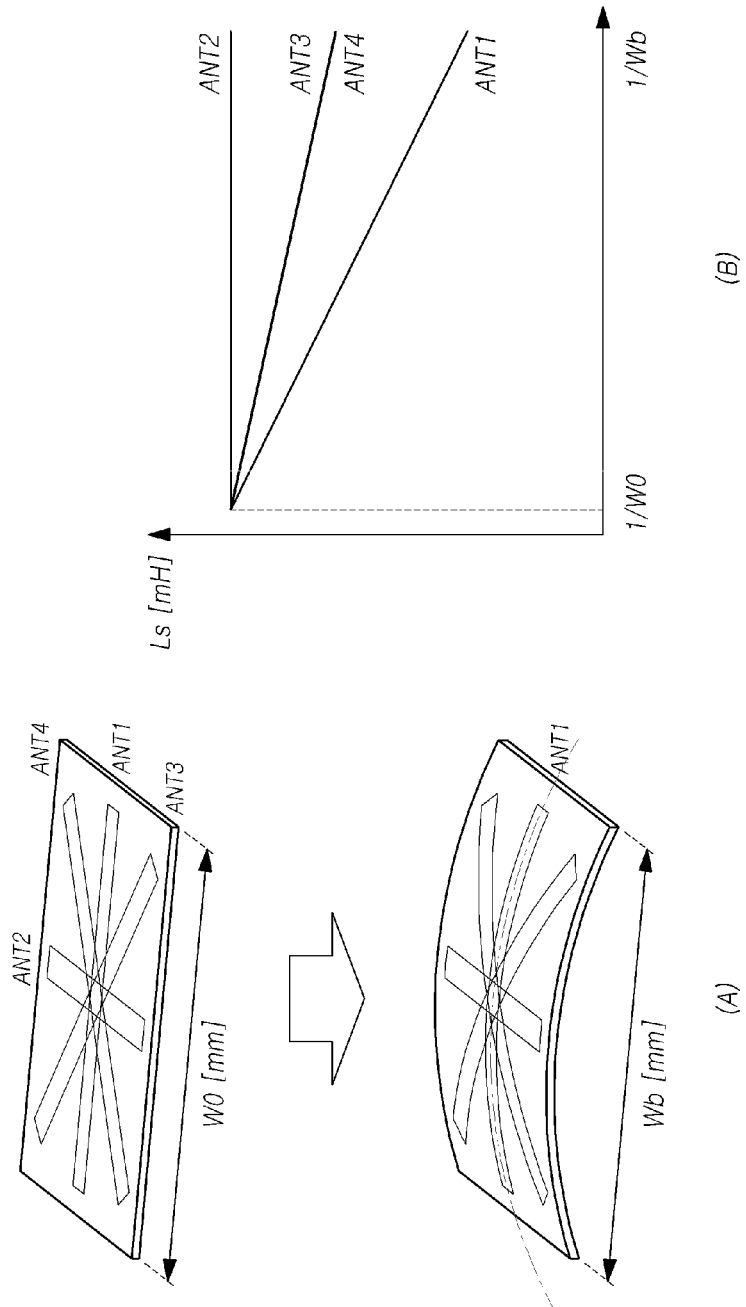
FIG. 7 is a view showing a change in a self-inductance measured according to a first bending type when the bending of the flexible device according to an embodiment of the present invention is detected based on self-inductances.

FIG. 7 is a view showing a change in a self-inductance measured according to a first bending type (a type in which the flexible device 100 is bent transversely or longitudinally) when bending of the flexible device 100 according to the embodiment of the present invention is detected based on a self-inductance (Ls).

FIG. 7A is a view showing a case in which the flexible device 100 having a transverse length W0 is bent transversely before bending.

With reference to FIG. 7A, as the flexible device 100 is bent transversely, the transverse line length of the flexible device 100 starts to become shorter than W0 [mm].

As the degree by which the flexible device 100 is bent transversely becomes larger, Wb [mm], which is a line length of the flexible device 100, gradually becomes shorter at W0 [mm].

In FIG. 7B, the x axis is an inverse number of a line length Wb of the flexible device 100, and represents a degree by which the flexible device 100 is bent transversely. The y axis represents self-inductances of the four antennas ANT1, ANT2, ANT3, and ANT4.

With reference to FIG. 7B, as a degree by which the flexible device 100 is bent transversely increases, that is, as an inverse number 1/Wb of a line length Wb of the flexible device 100 increases, a degree by which the self-inductance (Ls) [mH] is changed varies according to a degree by which the bending direction of the flexible device 100 corresponds to the disposition directions of the antennas.

With reference to FIG. 7B, as a degree by which the flexible device 100 is bent transversely increases, that is, as an inverse number 1/Wb of a transverse line length Wb of the flexible device 100 increases, a self-inductance measured in the antenna ANT1 disposed in a disposition direction (transverse direction) most corresponding to the bending direction (transverse direction) of the flexible device 100 decreases most.

That is, a change value ($\Delta Ls1 = Ls1 - Ls1'$) of the self-inductance measured in the antenna ANT1 becomes maximal. Here, Ls1 denotes a self-inductance measured in the antenna ANT1 before the flexible device 100 is bent, and Ls1' denotes a self-inductance measured in the antenna ANT1 after the flexible device 100 is bent.

With reference to FIG. 7B, as a degree by which the flexible device 100 is bent transversely increases, that is, as an inverse number 1/Wb of a transverse line length Wb of the flexible device 100 increases, a self-inductance measured in the antenna ANT1 disposed in a disposition direction (longitudinal direction) farthest from corresponding to the bending direction (transverse direction) of the flexible device 100 rarely decreases.

That is, a change value ($\Delta Ls2 = Ls2 - Ls2'$) of the self-inductance measured in the antenna ANT2 becomes minimal. Here, Ls2 denotes a self-inductance measured in the antenna ANT2 before the flexible device 100 is bent, and Ls2' denotes a self-inductance measured in the antenna ANT2 after the flexible device 100 is bent.

With reference to FIG. 7B, as a degree by which the flexible device 100 is bent transversely becomes larger, that is, an inverse number 1/Wb of a transverse line length Wb of the flexible device 100 becomes larger, the self-inductances measured in the antennas ANT3 and ANT4 disposed diagonally between the antenna ANT1 disposed in a disposition direction (transverse direction) most corresponding to the bending direction (transverse direction) of the flexible device 100 and the antenna ANT2 disposed in a disposition direction (longitudinal direction) farthest from corresponding to the bending direction (transverse direction) of the flexible device 100 decrease less than the decreased width of the self-inductance measured in the antenna ANT1 and decrease more than the decreased width of the self-inductance measured in the antenna ANT2.

That is, the change values ($\Delta Ls3 = Ls3 - Ls3'$, $\Delta Ls4 = Ls4 - Ls4'$) of the self-inductances measured in the antennas ANT3 and ANT4 are smaller than the change value ($\Delta Ls1 = Ls1 - Ls1'$) of the self-inductance measured in the antenna ANT1 and larger than the change value ($\Delta Ls2 = Ls2 - Ls2'$) of the self-inductance measured in the antenna ANT2. Here, Ls3 and Ls4 denote self-inductances measured in the antennas ANT3 and ANT4 before the flexible device 100 is bent, and Ls3' and LS4' denote self-inductances measured in the antennas ANT3 and ANT4 after the flexible device 100 is bent.

When the magnitudes of the change value (($\Delta Ls1$) of the self-inductance measured in the antenna ANT1, the change value (($\Delta Ls2$) of the self-inductance measured in the antenna ANT2, the change value (($\Delta Ls3$) of the self-inductance measured in the antenna ANT3, and the change value (($\Delta Ls4$) of the self-inductance measured in the antenna ANT4 are compared with each other, the following relationship is established.

$$\Delta Ls2 < \Delta Ls3 \approx \Delta Ls4 < \Delta Ls1$$

Meanwhile, the bending detection apparatus 200 for the flexible device 100 may store the change values of the self-inductances of the antennas according to a transverse bending strength 1/Wb as reference information.

Hereinafter, an example of detecting bending of the flexible device 100 when the flexible device 100 whose transverse line length before bending is W0 is bent transversely by a specific degree 1/Wb' will be described with reference to FIG. 8.

Figure 8:
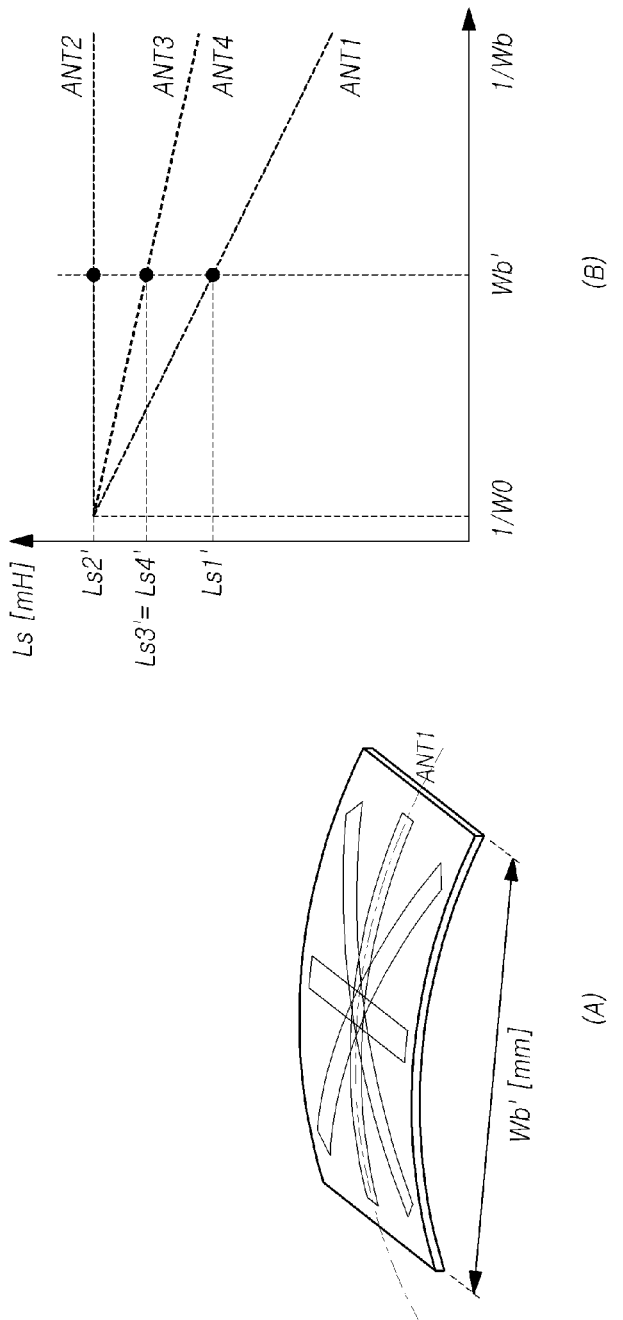
FIG. 8 is a view exemplifying that the bending (a first bending type) of the flexible device according to the present invention is detected based on self-inductance.

FIG. 8 is a view exemplifying that the bending (a first bending type) of the flexible device 100 according to the present invention is detected based on a self-inductance.

FIG. 8A is a view showing a state in which the flexible device whose transverse line length WO [mm] before bending is bent, and is a view showing that the flexible device 100 is bent transversely such that a transverse line length thereof is Wb' [mm].

FIG. 8B is a graph depicting the self-inductances measured in the four antennas ANT1 to ANT4 before and after the flexible device 100 is bent such that a transverse line length thereof is Wb' [mm].

With reference to FIG. 8B, the transverse line length of the flexible device 100 is WO before the flexible device 100 is bent, and then it is assumed that the self-inductances measured in the four antennas ANT1 to ANT4 are the same for convenience of description.

That is, it is assumed that the self-inductance Ls1 measured in the antenna ANT1, the self-inductance Ls2 measured in the antenna ANT2, the self-inductance Ls3 measured in the antenna ANT3, and the self-inductance Ls4 measured in the antenna ANT4 before the flexible device 100 is bent are all the same, that is, are Ls0.

With reference to FIG. 8B, the self-inductances measured in the four antennas ANT 1 to ANT4 after the flexible device 100 is bent such that a transverse line length thereof is Wb' [mm] may vary according to a degree by which the bending direction of the flexible device 100 corresponds to the disposition directions of the four antennas ANT1 to ANT4.

With reference to FIG. 8B, it may be identified that the self-inductance Ls1' measured in the antenna ANT1 disposed in a transverse direction which is a bending direction of the flexible device decreases most at Ls0 (=Ls1).

That is, the change value ΔLs1 of the self-inductance value of the antenna ANT1 before and after the flexible device 100 is bent is Ls0-Ls1'.

With reference to FIG. 8B, it may be identified that the self-inductance Ls2' measured in the antenna ANT2 disposed in a longitudinal direction which is farthest from corresponding to a bending direction of the flexible device, that is, a transverse direction is rarely changed at Ls0 (=Ls2).

That is, the change value ΔLs2 of the self-inductance of the antenna ANT2 before and after the flexible device 100 is bent is Ls0-Ls2', and because Ls2' and Ls0 are almost the same, ΔLs2 is close to zero.

With reference to FIG. 8B, it may be identified that the self-inductances Ls3' and Ls4' measured in the antennas ANT3 and ANT4 disposed in diagonal directions between a transverse direction which is a bending direction of the flexible device 100 and a longitudinal direction which is a direction farthest from corresponding to the transverse direction are rarely changed at Ls0 (=Ls2).

That is, because the change value ΔLs3 of the self-inductance of the antenna ANT3 before and after the flexible device 100 is bent is Ls0-Ls3' and Ls3' is larger than Ls2' and smaller than Ls1', ΔLs3 is a value between ΔLs2 and ΔLs1.

Likewise, because the change value ΔLs4 of the self-inductance of the antenna ANT4 before and after the flexible device 100 is bent is Ls0-Ls4' and Ls4' is larger than Ls2' and smaller than Ls1', ΔLs4 is a value between ΔLs2 and ΔLs1.

With reference to FIG. 8B, if the change values of the self-inductances of the antennas ANT1, ANT2, ANT3, and ANT4 before and after the flexible device 100 is bent, the following relationship is established.

$$\Delta Ls2 < \Delta Ls3 \approx \Delta Ls4 < \Delta Ls1$$

Thus, a disposition direction of the antenna ANT1 which is an antenna whose change value of self-inductances is the largest before and after the flexible device 100 is bent, that is, a transverse direction may be determined as a bending direction of the flexible device 100.

Further, as an example, the bending detection unit 220 determines a bending strength of the flexible device 100 to be 1/Wb' by comparing the change values of the self-inductances measured in the antennas before and after the flexible device 100 is bent with the change values (dotted lines of FIG. 8B) of the self-inductances according to bending strengths (1/Wb) for the antennas corresponding to reference information stored in advance.

With reference to FIG. 8, when the flexible device 100 is bent longitudinally as in the above-described method, bending may be detected by determining a bending direction, a bending strength, and the like.

Hereinafter, as a second bending type, self-inductances (Ls) measured in the antennas ANT1, ANT2, ANT3, and ANT4 while a degree (bending strength) by which the flexible device 100 is bent diagonally is changed will be described with reference to FIG. 9, and an example of detecting bending of the flexible device 100 when the flexible device 100 is bent diagonally by a specific degree will be described with reference to FIG. 10.

Figure 9:
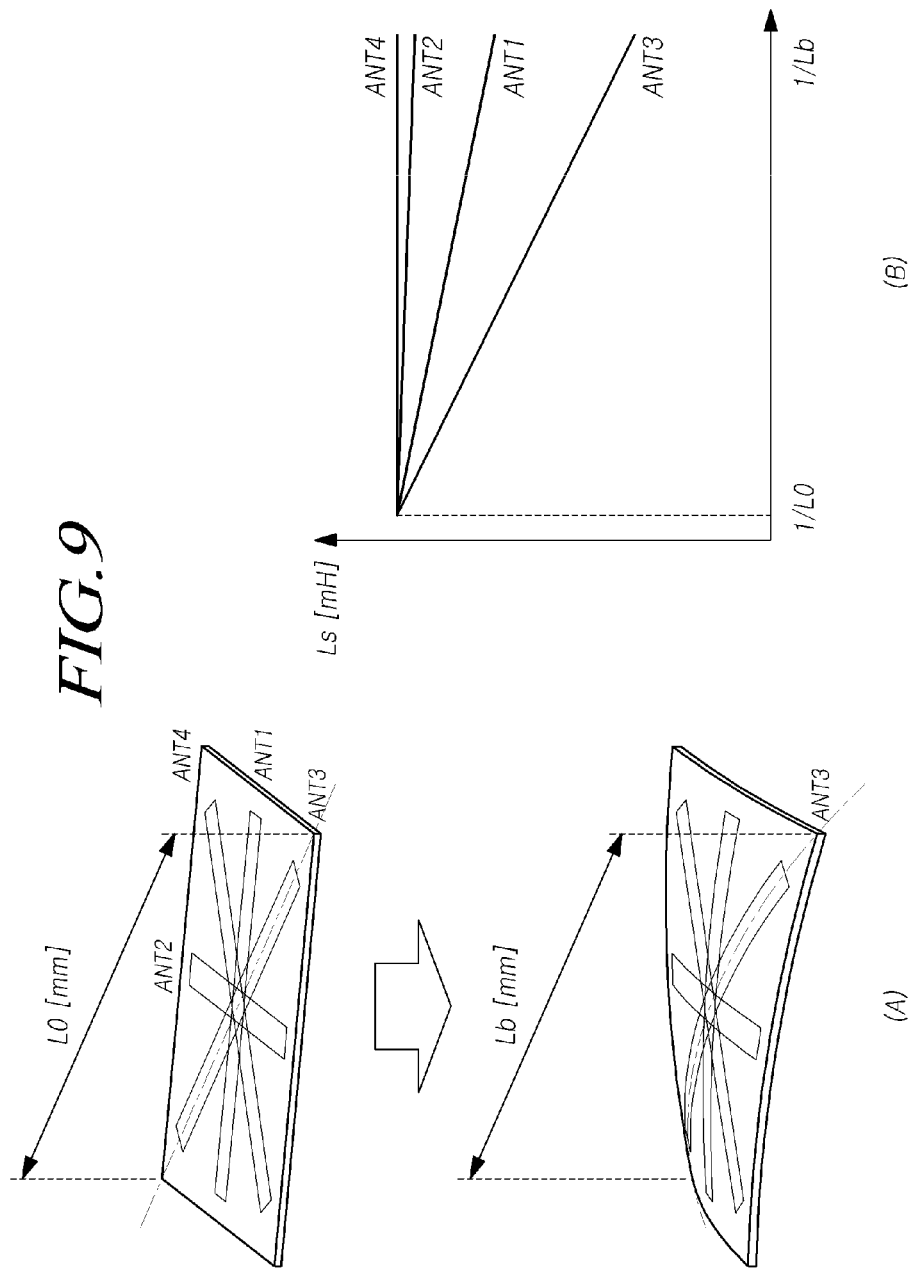
FIG. 9 is a view showing a change in a self-inductance measured according to a second bending type when the bending of the flexible device according to an embodiment of the present invention is detected based on self-inductances.

FIG. 9 is a view showing a change in a self-inductance measured according to a second bending type (twisting) when the bending of the flexible device 100 according to an embodiment of the present invention is detected based on self-inductances.

FIG. 9A is a view showing that the flexible device having a length of L0 is bent in a diagonal direction corresponding to the disposition direction of the antenna ANT3 before bending, that is, a diagonal direction (↘) from the upper left end to the lower right end.

With reference to FIG. 9A, as the flexible device 100 is bent diagonally, the diagonal line length of the flexible device 100 starts to become shorter than L0 [mm].

As the degree by which the flexible device 100 is bent diagonally becomes larger, Lb [mm] which is a diagonal line length of the flexible device 100 gradually becomes shorter at L0 [mm].

In FIG. 9B, the x axis is an inverse number of a diagonal line length Lb of the flexible device 100, and represents a degree by which the flexible device 100 is bent diagonally. The y axis represents self-inductances (Ls) measured in the four antennas ANT1, ANT2, ANT3, and ANT4.

With reference to FIG. 9B, as a degree by which the flexible device 100 is bent diagonally increases, that is, as an inverse number 1/Lb of a diagonal line length Lb of the flexible device 100 increases, a degree by which the self-inductance (Ls) [mH] is changed varies according to a degree by which the bending direction (diagonal direction) of the flexible device 100 corresponds to the disposition directions of the antennas.

With reference to FIG. 9B, as a degree by which the flexible device 100 is bent diagonally increases, that is, as an inverse number 1/Lb of a diagonal line length Lb of the flexible device 100 increases, a self-inductance measured in the antenna ANT3 disposed in a disposition direction (diagonal direction) most corresponding to the bending direction (diagonal direction) of the flexible device 100 decreases the most.

That is, a change value (ΔLs3=Ls3−Ls3') of the self-inductance measured in the antenna ANT3 becomes maximal. Here, Ls3 denotes a self-inductance measured in the antenna ANT3 before the flexible device 100 is bent, and Ls3' denotes a self-inductance measured in the antenna ANT3 after the flexible device 100 is bent.

With reference to FIG. 9B, as a degree by which the flexible device 100 is bent in a diagonal direction from the upper left end to the lower right end increases, that is, as an inverse number 1/Lb of a diagonal line length Lb in the diagonal direction of the flexible device 100 increases, a self-inductance measured in the antenna ANT4 disposed in a disposition direction (a diagonal direction from a lower left end to an upper right end) farthest from corresponding to the bending direction (diagonal direction) of the flexible device 100 is changed by the smallest width.

That is, a change value (ΔLs4=Ls4−Ls4') of the self-inductance measured in the antenna ANT4 becomes minimal. Here, Ls4 denotes a self-inductance measured in the antenna ANT4 before the flexible device 100 is bent, and Ls4' denotes a self-inductance measured in the antenna ANT4 after the flexible device 100 is bent.

With reference to FIG. 9B, as a degree by which the flexible device 100 is bent in a diagonal direction from the upper left end to the lower right end becomes larger, that is, an inverse number 1/Lb of a diagonal line length Lb of the flexible device 100 becomes larger, the self-inductances measured in the antennas ANT3 and ANT4 disposed in a diagonal direction between the antenna ANT3 disposed in a disposition direction (a diagonal direction from the upper left end to the lower right end) most corresponding to the bending direction of the flexible device 100 and the antenna ANT4 disposed in a disposition direction (a diagonal direction from the lower left end to the upper right end) farthest from corresponding to the bending direction of the flexible device 100 decreases by a width smaller than a decreased width of the self-inductance measured in the antenna ANT3 and decreases by a width larger than a decreased width of the self-inductance measured in the antenna ANT4.

That is, the change values (ΔLs1=Ls1−Ls1', ΔLs2=Ls2−Ls2') measured in the antennas ANT1 and ANT2 are smaller than the change value (ΔLs3=Ls3−Ls3') of the self-inductance measured in the antenna ANT3 and larger than the change value (ΔLs4=Ls4−Ls4') of the self-inductance measured in the antenna ANT4. Here, Ls1 and Ls2 denote self-inductances measured in the antennas ANT1 and ANT2 before the flexible device 100 is bent, and Ls1' and LS2' denote self-inductances measured in the antennas ANT1 and ANT2 after the flexible device 100 is bent.

When the magnitudes of the change value ((ΔLs1) of the self-inductance measured in the antenna ANT1, the change value ((ΔLs2) of the self-inductance measured in the antenna ANT2, the change value ((ΔLs3) of the self-inductance measured in the antenna ANT3, and the change value ((ΔLs4) of the self-inductance measured in the antenna ANT4 are compared with each other, the following relationship is established.

$$\Delta Ls4 < \Delta Ls2 < \Delta Ls1 < Ls3$$

Meanwhile, the bending detection apparatus 200 for the flexible device 100 may store the change values of the self-inductances of the antennas according to a diagonal bending strength 1/Lb as reference information.

Hereinafter, an example of detecting bending of the flexible device 100 when the flexible device 100 whose diagonal line length before bending is L0 is bent in a diagonal direction of the flexible device 100 by a specific degree 1/Lb' will be described with reference to FIG. 10.

Figure 10:
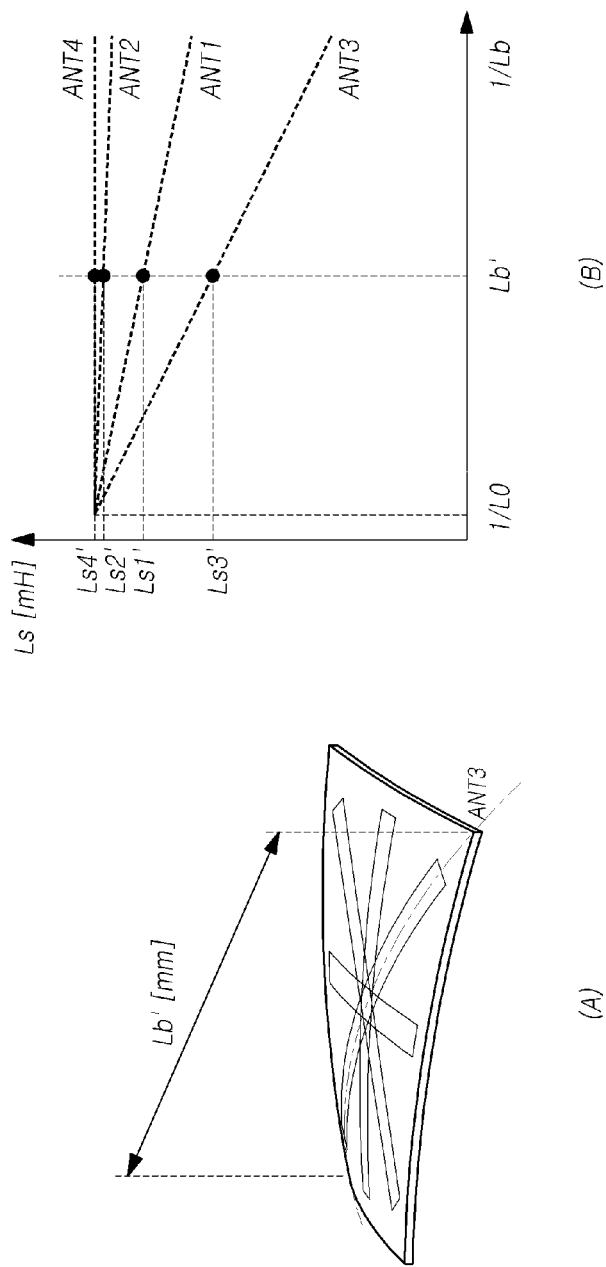
FIG. 10 is a view exemplifying that the bending (a second bending type) of the flexible device according to the present invention is detected based on self-inductance.

FIG. 10 is a view exemplifying that the bending (a second bending type) of the flexible device 100 according to the present invention is detected based on a self-inductance.

FIG. 10A is a view showing a state in which the flexible device whose diagonal line length L0 [mm] before bending is bent, and is a view showing that the flexible device 100 is bent in a diagonal direction from an upper left end to a lower right end such that a diagonal line length thereof is Lb' [mm].

FIG. 10B is a graph depicting the self-inductances measured in the four antennas ANT1 to ANT4 before and after the flexible device 100 is bent such that a diagonal line length thereof from an upper left end to a lower right end is Lb' [mm].

With reference to FIG. 10B, the diagonal line length of the flexible device 100 from an upper left end to a lower right end is L0 before the flexible device 100 is bent, and then it is assumed that the self-inductances measured in the four antennas ANT1 to ANT4 are the same for convenience of description.

That is, it is assumed that the self-inductance Ls1 measured in the antenna ANT1, the self-inductance Ls2 measured in the antenna ANT2, the self-inductance Ls3 measured in the antenna ANT3, and the self-inductance Ls4 measured in the antenna ANT4 before the flexible device 100 is bent are all the same, that is, are Ls0.

With reference to FIG. 10B, the self-inductances measured in the four antennas ANT 1 to ANT4 after the flexible device 100 is bent such that a diagonal line length thereof from an upper left end to a lower right end is Lb' [mm] may vary according to a degree by which the bending direction of the flexible device 100 corresponds to the disposition directions of the four antennas ANT1 to ANT4.

With reference to FIG. 10B, the self-inductance Ls3' measured in the antenna ANT3 disposed in a diagonal direction from an upper left end to a lower right end which is a bending direction of the flexible device decreases most at Ls0 (=Ls3).

That is, the change value ΔLs3 of the self-inductance value of the antenna ANT3 before and after the flexible device 100 is bent is Ls0-Ls3'.

With reference to FIG. 10B, it may be identified that the self-inductance Ls4' measured in the antenna ANT4 disposed in a direction (a diagonal direction from a lower left end to an upper right end) which is farthest from corresponding to a diagonal direction of the flexible device from an upper left end to a lower right end which is a bending direction is rarely changed at Ls0 (=Ls4).

That is, the change value ΔLs4 of the self-inductance of the antenna ANT4 before and after the flexible device 100 is bent is Ls0-Ls4', and because Ls4' and Ls0 are almost the same, ΔLs4 is close to 0 (zero).

With reference to FIG. 10B, the self-inductances Ls1' and Ls2' measured in the antennas ANT1 and ANT2 disposed in a transverse direction and a longitudinal direction between a diagonal direction from an upper left end to a lower right end and a diagonal direction from an upper left end to an upper right end, which are bending directions of the flexible device 100, are decreased by a width smaller than a decreased width of the self-inductance of the antenna ANT3 and are decreased by a width larger than a decreased width of the self-inductance of the antenna ANT4.

That is, because the change value ΔLs1 of the self-inductance of the antenna ANT1 before and after the flexible device 100 is bent is Ls0-Ls1' and Ls1' is larger than Ls4' and smaller than Ls3', ΔLs1 is a value between ΔLs4 and ΔLs3.

Likewise, because the change value ΔLs2 of the self-inductance of the antenna ANT2 before and after the flexible device 100 is bent is Ls0-Ls2' and Ls2' is larger than Ls4' and smaller than Ls3', ΔLs2 is a value between ΔLs4 and ΔLs3.

With reference to FIG. 10B, if the change values of the self-inductances of the antennas ANT1, ANT2, ANT3, and ANT4 before and after the flexible device 100 is bent, the following relationship is established.

$$\Delta Ls4 < \Delta Ls2 < \Delta Ls1 < \Delta Ls3$$

Thus, a disposition direction of the antenna ANT3 which is an antenna whose change value of self-inductances is the largest before and after the flexible device 100 is bent, that is, a diagonal direction from a lower left end to an upper right end may be determined as the bending direction of the flexible device 100.

Further, as an example, the bending detection unit 220 may determine the bending strength of the flexible device 100 to be 1/Lb' by comparing the change values of the self-inductances measured in the antennas before and after the flexible device 100 is bent with the change values (dotted lines of FIG. 10B) of the self-inductances according to bending strengths (1/Lb) for the antennas corresponding to reference information stored in advance.

Until now, the bending detection method based on a self-inductance (Ls) and an antenna disposition pattern in the method has been described, and hereinafter, a bending detection method based on mutual inductance (Lm) and an antenna disposition pattern then will be described in more detail with reference to FIGS. 11 to 17.

Figure 11:
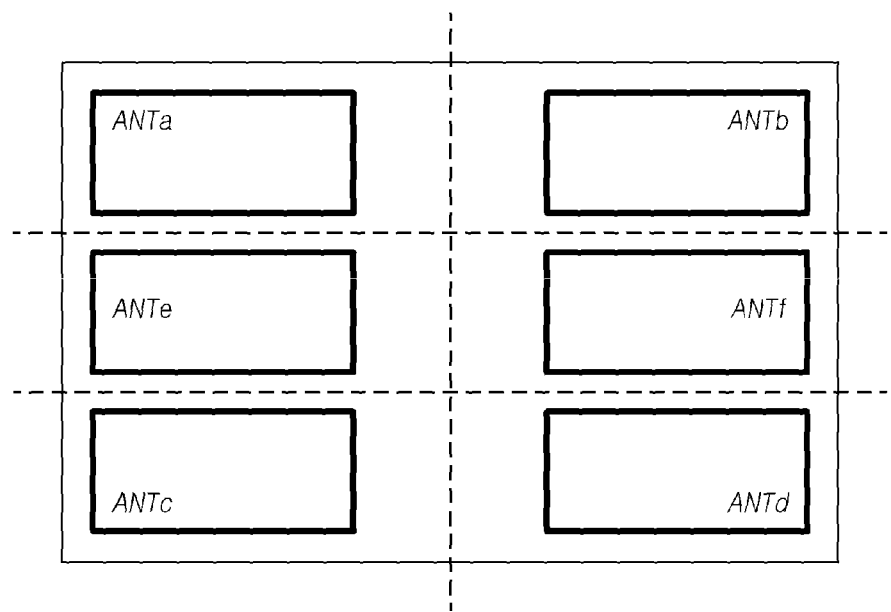
FIG. 11 is an exemplary view of the disposition of antennas when bending of the flexible device 100 according to the embodiment of the present invention is detected based on mutual inductance.

FIG. 11 is an exemplary view of the disposition of antennas when bending of the flexible device 100 according to the embodiment of the present invention is detected based on a mutual inductance (Lm).

With reference to FIG. 11, when the bending detection unit 220 detects bending of the flexible device 100 based on mutual inductances of a plurality of antennas, that is, a plurality of antennas ANTa, ANTb, ANTc, . . . include three or more antennas such that two or more pairs of antennas include a combination of a first antenna and a second antenna selected from the plurality of antennas ANTa, ANTb, ANTc, . . . included in the antenna unit 210.

Here, the first antenna pertains to a primary circuit to which a current or a voltage is supplied to measure a mutual inductance, and the second antenna is an antenna that pertains to a secondary circuit and is an antenna in which a voltage according to a change in current in the first antenna pertaining to the primary circuit or a mutual inductance is measured.

The pair of antennas formed by the plurality of antennas ANTa, ANTb, ANTc, . . . exemplified in FIG. 11 may be a pair of antennas in which the first antenna and the second antenna are the antennas ANTa and ANTb, a pair of antennas in which the first antenna and the second antenna are the antennas ANTa and ANTf, a pair of antennas in which the first antenna and the second antenna are the antennas ANTa and ANTd, a pair of antennas in which the first antenna and the second antenna are the antennas ANTa and ANTe, a pair of antennas in which the first antenna and the second antenna are the antennas ANTa and ANTc, a pair of antennas in which the first antenna and the second antenna are the antennas ANTb and ANTe, a pair of antennas in which the first antenna and the second antenna are the antennas ANTb and ANTc, or the like.

Because the number of the plurality of antennas ANTa, ANTb, ANTc, . . . exemplified in FIG. 11 is six, the maximum number of the pairs of antennas which can be produced is $_6C_2 = 6!/(4!2!) = 15$.

As shown in FIG. 11, the plurality of antennas ANTa, ANTb, ANTc, . . . are disposed such that the disposition areas thereof are different from each other.

In this way, in order that the plurality of antennas ANTa, ANTb, ANTc, . . . are disposed such that the disposition areas thereof are different from each other, for example, the plurality of antennas ANTa, ANTb, ANTc, . . . are disposed in areas divided by one or more vertical lines or one or more horizontal lines of the flexible device 100 such that the disposition areas thereof are different from each other.

Further, in order that the plurality of antennas ANTa, ANTb, ANTc, . . . are disposed such that the disposition areas thereof are different from each other, for example, directions from the first antennas to the second antennas of the two or more pairs of antennas formed by the plurality of antennas ANTa, ANTb, ANTc, . . . are made different such that the disposition areas thereof are different from each other.

Meanwhile, with reference to FIG. 11, the first antennas and the second antennas of the two or more antennas including a combination of a first antenna and a second antenna selected from the plurality of antennas ANTa, ANTb, ANTc, . . . may be symmetrical to each other.

For example, in the pair of antennas in which the first antenna and the second antenna are the antennas ANTa and ANTb, the first antenna and the second antenna ANTa and the ANTb are line-symmetrical to each other with respect to a vertical line. Further, in the pair of antennas in which the first antenna and the second antenna are the antennas ANTa and ANTc, the first antenna and the second antenna ANTa and the ANTc are line-symmetrical to each other with respect to a horizontal line (one of the two horizontal lines of FIG. 11). Further, in the pair of antennas in which the first antenna and the second antenna are the antennas ANTa and ANTd, the first antenna and the second antenna ANTa and the ANTd are point-symmetrical to each other with respect to the center of the flexible device 100.

Meanwhile, with reference to FIG. 11, as a change in a distance between the first antenna and the second antenna forming at least one pair of antennas of the two or more pairs of antennas becomes larger than a change in a distance between the first antenna and the second antenna forming the remaining pairs of antennas, a larger number of antennas may be disposed.

For example, with reference to FIG. 11, when the flexible device 100 is transversely bent with respect to a vertical line, a distance between the antennas ANTa and ANTb of the pair of antennas in which the first antenna and the second antenna are the antennas ANTa and ANTb is decreased by a degree smaller than a degree by which a distance between the antennas ANTa and ANTc of the pair of antennas in which the first antenna and the second antenna are the antennas ANTa and ANTc is decreased. That is, a change in a distance between the antennas ANTa and ANTb in the pair of antennas in which the first antenna and the second antenna are the antennas ANTa and ANTb is larger than a change in a distance between the antennas ANTa and ANTc in the pair of antennas in which the first antenna and the second antenna are the antennas ANTa and ANTc.

As shown in FIG. 11, the plurality of antennas ANTa, ANTb, ANTc, . . . may be ring-shaped loop antennas.

According to the antenna disposition characteristics, if the flexible device 100 is bent in a specific direction, the plurality of antennas ANT1, ANT2, . . . also are bent. However, the bending degrees of the plurality of antennas ANT1, ANT2, . . . may be different according to the unique disposition directions thereof.

Accordingly, before and after the flexible device 100 is bent, the change values of the mutual inductances measured in the two or more pairs of antennas of the plurality of antennas ANT1, ANT2, . . . vary according to the degrees by which the plurality of antennas ANT1, ANT2, . . . are bent.

For example, the change values of the mutual inductances measured in the pair of antennas of the two or more pairs of antennas including the plurality of antennas ANT1, ANT2, . . . , in which the direction from the first antenna to the second antenna most corresponds to the bending direction of the flexible device 100, is maximal.

Figure 12:
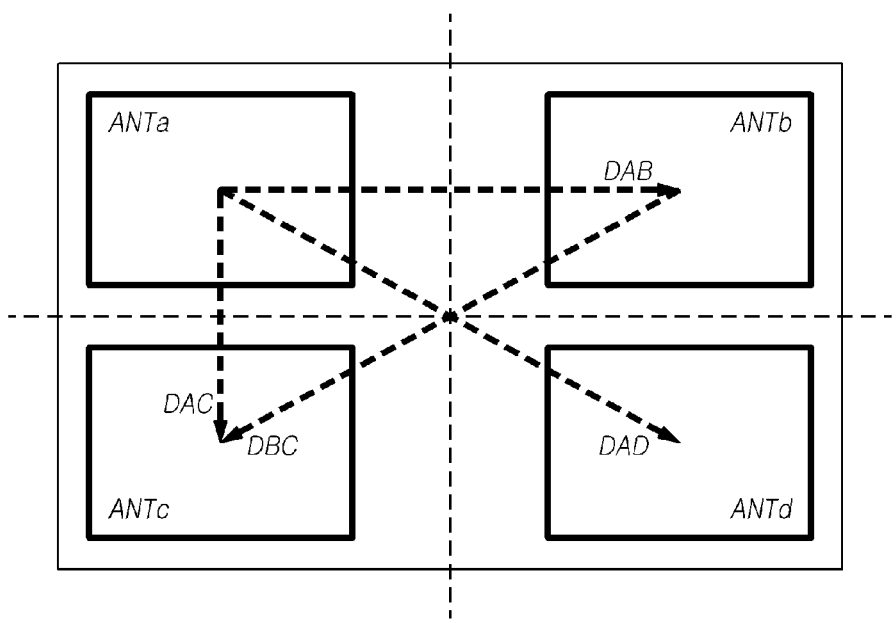
FIG. 12 is another exemplary view of the disposition of antennas when bending of the flexible device 100 according to the embodiment of the present invention is detected based on mutual inductance.

Although FIG. 11 exemplifies that the number of antennas is six, it is merely an example for the convenience of description and three or more antennas may be variously designed. FIG. 12 exemplifies that the number of antennas is four.

FIG. 12 is another exemplary view of the disposition of antennas when bending of the flexible device 100 according to the embodiment of the present invention is detected based on mutual inductance (Lm).

FIG. 12 is a view showing the antenna unit 210 when the number of antennas is four in FIG. 11, that is, the antenna unit 210 including four antennas ANTa, ANTb, ANTc, and ANTd.

With reference to FIG. 12, the antenna unit 210 includes an antenna ANTa disposed in a first quadrant of the flexible device 100, an antenna ANTb disposed in a second quadrant of the flexible device 100, an antenna ANTc disposed in a third quadrant of the flexible device 100, and an antenna ANTd disposed in a fourth quadrant of the flexible device 100.

With reference to FIG. 12, the pair of antennas produced by selecting a first antenna and a second antenna from the four antennas ANTa, ANTb, ANTc, and ANTd may include a pair of antennas ANTa-ANTb in which the first antenna and the second antenna are the antennas ANTa and ANTb, a pair of antennas ANTa-ANTd in which the first antenna and the second antenna are the antennas ANTa and ANTd, a pair of antennas ANTa-ANTc in which the first antenna and the second antenna are the antennas ANTa and ANTc, and a pair of antennas ANTb-ANTc in which the first antenna and the second antenna are the antennas ANTb and ANTc, and the maximum number of the pairs of antennas may be $_4C_2 = 4!/(2!2!) = 6$. Hereinafter, as an example, only four pairs of antennas will be described.

A direction from the first antenna to the second antenna in the pair of antennas ANTa-ANTb in which the first antenna and the second antenna are the antennas ANTa and ANTb is a transverse direction Dab, a direction from the first antenna to the second antenna in the pair of antennas ANTa-ANTd in which the first antenna and the second antenna are the antennas ANTa and ANTd is a diagonal direction Dad from an upper left end to a lower right end, a direction from the first antenna to the second antenna in the pair of antennas ANTa-ANTc in which the first antenna and the second antenna are the antennas ANTa and ANTc is a longitudinal direction Dac, and a direction from the first antenna to the second antenna in the pair of antennas ANTb-ANTc in which the first antenna and the second antenna are the antennas ANTb and ANTc is a diagonal direction Dbc from an upper right end to a lower left end.

Hereinafter, a method of detecting bending of the flexible device 100 which has the antenna disposition pattern shown in FIG. 12 based on a mutual inductance will be described in more detail with reference to FIGS. 13 to 17.

Figure 13:
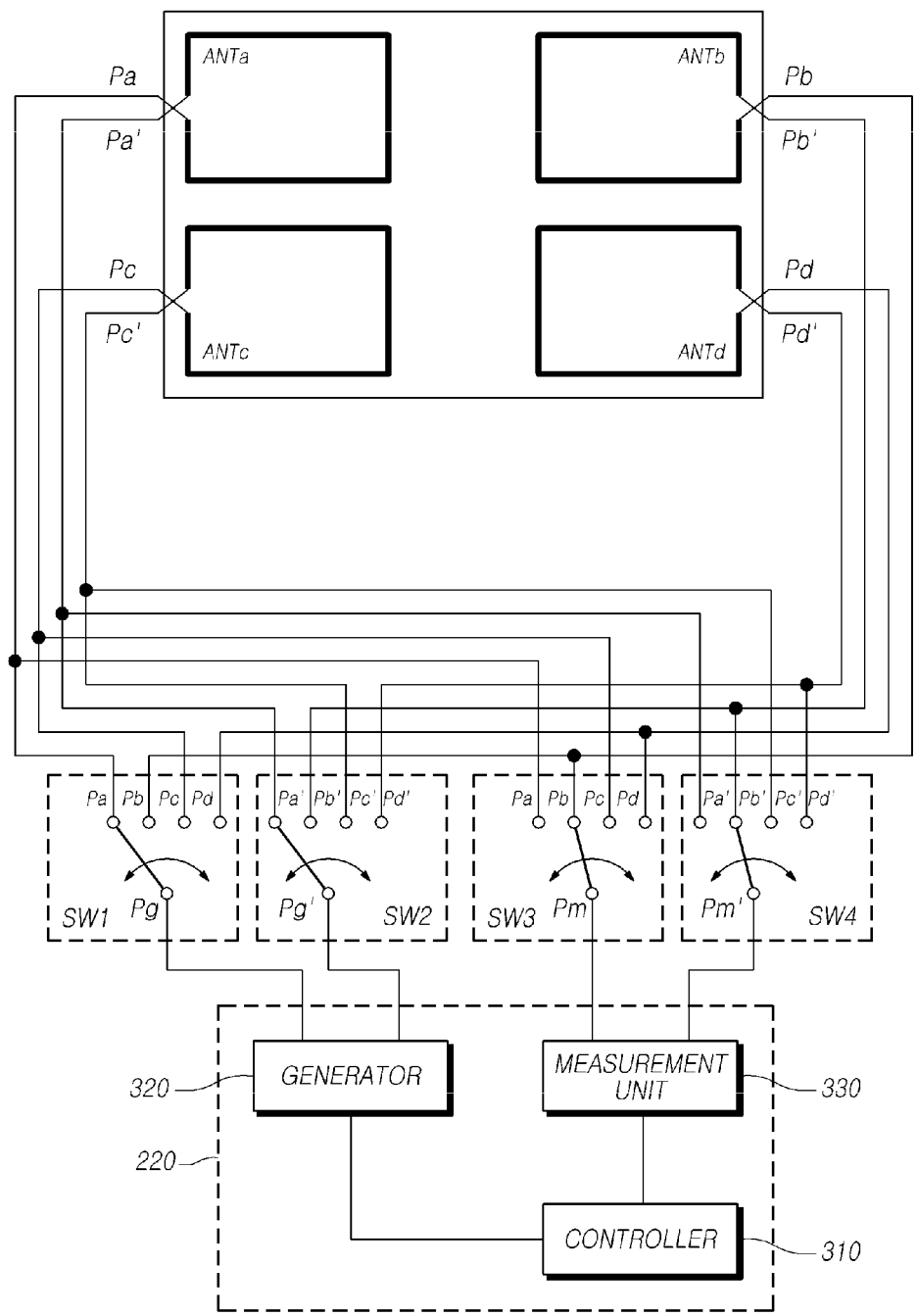
FIG. 13 is a view showing a connection structure of an antenna unit and a bending detection unit when bending of a flexible device is detected based on mutual inductance according to an embodiment of the present invention.

FIG. 13 is a view showing a connection structure of the antenna unit 210 and the bending detection unit 220 when bending of the flexible device 100 according to the embodiment of the present invention is detected based on a mutual inductance (Lm).

With reference to FIG. 13, each of the four antennas ANTa, ANTb, ANTc, and ANTd having different disposition areas has two ports, the two ports are connected to two ports Pg and Pg' of the generator 320 through the two switches SW1 and SW2 and are connected to the two ports Pm and Pm' of the measurement unit 330 through the two switches SW3 and SW4.

Each of the four antennas ANTa, ANTb, ANTc, and ANTd receives a current or a voltage from the generator 320 through the two ports and a voltage or a mutual inductance is measured by the measurement unit 330.

FIG. 13 is a view showing that a mutual inductance of the pair of antennas ANTa-ANTb in which the first antenna and the second antenna are the antennas ANTa and ANTb is measured.

In order to select the antenna ANTa as the first antenna, the switch SW1 connects the port Pg and the port Pa of the antenna ANTa and the switch SW2 connects the port Pg' and the port Pa' of the antenna ANTa. Accordingly, a primary circuit including the antenna ANTa is produced.

In order to select the antenna ANTb as the second antenna, the switch SW2 connects the port Pm and the port Pb of the antenna ANTb and the switch SW4 connects the port Pm' and the port Pb' of the antenna ANTb. Accordingly, a secondary circuit including the antenna ANTb is produced.

The antenna may be selected by controlling operations of the four switches SW1 to SW4 by the controller 310.

In this way, the antenna ANTa and the antenna ANTb are selected as the first antenna and the second antenna to form the pair of antennas ANTa-ANTb, the generator 320 supplies a current or a voltage to the antenna ANTa, and a voltage or a mutual inductance induced in the secondary circuit including the antenna ANTb according to a change in current in the primary circuit including the antenna ANTa is measured by the measurement unit 330.

In this way, the measurement unit 330 measures the mutual inductances of the pairs of antennas ANTa-ANTb, ANTa-ANTd, ANTa-ANTc, and ANTb-ANTc before and after the flexible device 100 is bent. The mutual inductances measured by the measurement unit 330 may be stored.

The bending detection unit 220 may recognize change values of the mutual inductances of two or more pairs of antennas before and after the flexible device 100 is bent, compare the recognized change values of the mutual inductances of the two or more pairs of antennas, and determine a bending direction of the flexible device 100 based on the comparison result and directions of first antennas to second antennas forming the two or more pairs of antennas.

In this regard, the mutual inductance of the pair of antennas, of the two or more pairs of antennas, in which a direction from the first antenna to the second antenna most corresponding to the bending direction of the flexible device 100 increases most after the flexible device 100 is bent.

Thus, the change value of the mutual inductance of the pair of antennas, of the two or more pairs of antennas, in which a direction from the first antenna to the second antenna most corresponding to the bending direction of the flexible device 100 before and after the flexible device 100 is bent may be maximal.

Based on this fact, a pair of antennas of which the change value of the mutual inductance is maximal before and after the flexible device 100 is bent is identified such that a direction from the first antenna to the second antenna forming the identified pair of antennas may be determined as the bending direction of the flexible device 100.

Meanwhile, the controller 310 of the bending detection unit 220 may determine a bending strength of the flexible device 100 based on the magnitudes of the recognized change values of the mutual inductances of the two or more pairs of antennas.

Hereinafter, mutual inductances (Lm) measured in the antennas ANTa to ANTc and change values thereof while a degree (bending strength) by which the flexible device 100 is bent transversely will be described with reference to FIG. 14, and an example of detecting bending of the flexible device 100 when the flexible device 100 is bent transversely by a specific degree will be described with reference to FIG. 15.

Further, mutual inductances (Lm) measured in the antennas ANTa to ANTc and change values thereof while a degree (bending strength) by which the flexible device 100 is bent diagonally will be described with reference to FIG. 16, and an example of detecting bending of the flexible device 100 when the flexible device 100 is bent diagonally by a specific degree will be described with reference to FIG. 17.

Figure 14:
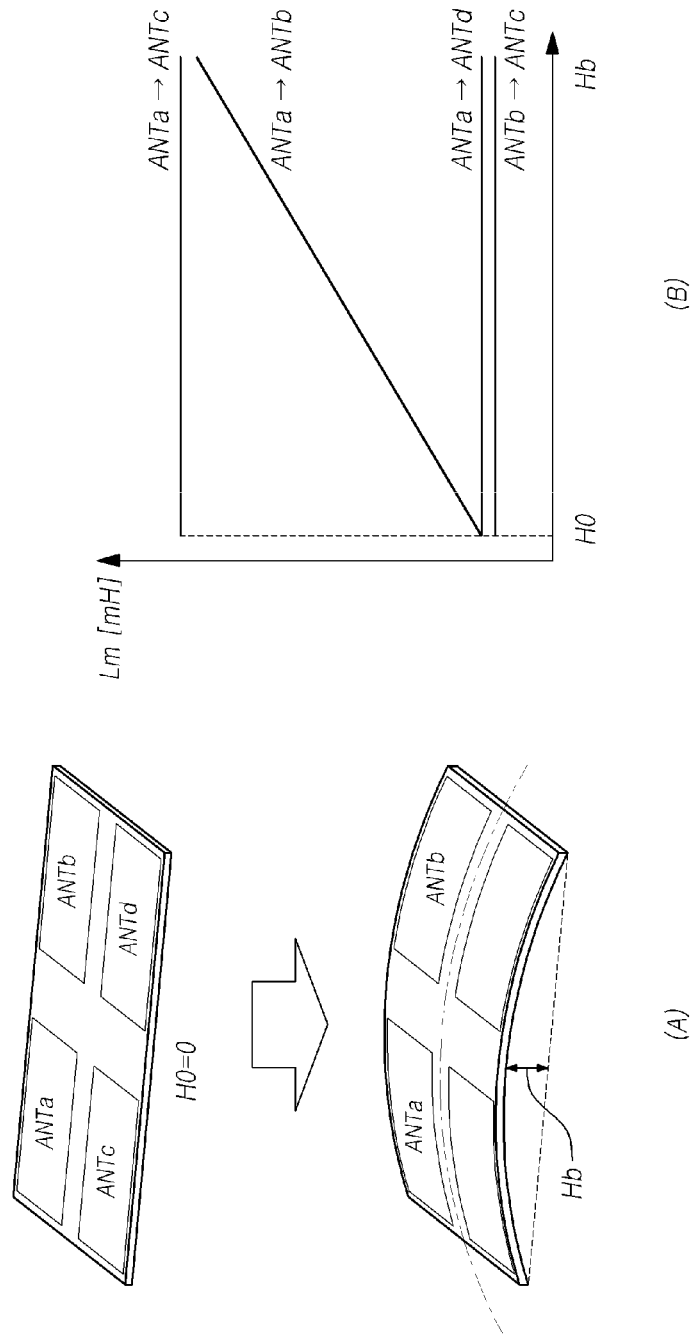
FIG. 14 is a view showing a change in a mutual inductance measured according to a first bending type when the bending of the flexible device according to an embodiment of the present invention is detected based on mutual inductances.

FIG. 14 is a view showing a change in a mutual inductance measured according to a first bending type in which the flexible device 100 is bent transversely when the bending of the flexible device 100 according to an embodiment of the present invention is detected based on mutual inductances.

FIG. 14A is a view showing that a flat flexible device 100 is bent transversely, and in a description related to detection of bending based on mutual inductance, the bending state is expressed by a maximum height H from the horizontal surface to the flexible device 100.

With reference to FIG. 14A, the height from the horizontal surface before the flexible device 100 is bent is H0=0 [mm], and as the flexible device 100 is bent transversely, the maximum height (Hb) from the horizontal surface to the flexible device 100 becomes larger than H0 [mm].

That is, as the degree by which the flexible device 100 is bent transversely becomes larger, the maximum height (Hb [mm]) from the horizontal surface to the flexible device 100 gradually becomes larger from H0 [mm].

In FIG. 14B, the x axis is a maximum height Hb from the horizontal surface to the flexible device 100, and represents a degree (bending strength) by which the flexible device 100 is bent transversely. The y axis represents mutual inductances (Lm) measured in the four pairs of antennas ANTa-ANTb, ANTa-ANTd, ANTa-ANTc, and ANTb-ANTc formed by the four antennas ANTa to ANTd, and may be voltages (corresponding to the mutual inductances) measured in the pairs of antennas ANTa-ANTb, ANTa-ANTd, ANTa-ANTc, and ANTb-ANTc formed by the four antennas ANTa to ANTd.

With reference to FIG. 14B, as a degree by which the flexible device 100 is bent transversely becomes higher, that is, a maximum height (Hb) from the horizontal surface to the flexible device 100 becomes larger, a degree by which the mutual inductance (Lm [mH]) is changed varies according to a degree by which the bending direction of the flexible device 100 corresponds to a direction Dab, Dad, Dac, and Dbc between the first antenna and the second antenna forming the pairs of antennas ANTa-ANTb, ANTa-ANTd, ANTa-ANTc, and ANTb-ANTc.

With reference to FIG. 14B, as a degree by which the flexible device 100 is bent transversely becomes higher, that is, a maximum height (Hb) from the horizontal surface to the flexible device 100 becomes larger, the mutual inductance measured in the pairs of antennas ANTa-ANTb, of the considered four pairs of antennas ANTa-ANTb, ANTa-ANTd, ANTa-ANTc, and ANTb-ANTc in which the first antenna and the second antenna are disposed to most correspond to a transverse direction which is a bending direction of the flexible device 100 increases most.

That is, the change value ($\Delta Lm(a\text{-}b) = Lm(a\text{-}b)' - Lm(a\text{-}b)$) of the mutual inductance measured in the pairs of antennas ANTa-ANTb in which the first antenna and the second antenna are the antennas ANTa and ANTb. Here, Lm(a-b) is a mutual inductance measured in the pair of antennas ANTa-ANTb in which the first antenna and the second antenna are the antennas ANTa and ANTb, and Lm(a-b)' is a mutual inductance measured in the pair of antennas ANTa-ANTb in which the first antenna and the second antenna are the antennas ANTa and ANTb after the flexible device 100 is bent and may be a value larger than Lm(a-b).

With reference to FIG. 14B, as a degree by which the flexible device 100 is bent transversely becomes higher, that is, a maximum height (Hb) from the horizontal surface to the flexible device 100 becomes larger, the change of the mutual inductance measured in the pairs of antennas ANTa-ANTb, of the considered four pairs of antennas ANTa-ANTb, ANTa-ANTd, ANTa-ANTc, and ANTb-ANTc in which the first antenna and the second antenna are disposed to be farthest from corresponding to a bending direction (a transverse direction) of the flexible device 100 is a mere value.

Although the change values of the mutual inductances measured in the antennas ANTa-ANTd, ANTa-ANTc, and ANTb-ANTc may actually be small values, FIG. 14B conceptually shows that there is no change in the values for convenience of description.

Meanwhile, the bending detection apparatus 200 for the flexible device 100 may store the change values of the mutual inductances of the antennas according to a transverse bending strength Hb as reference information.

Hereinafter, an example of detecting bending of the flexible device 100 when a flat flexible device 100 is bent by a predetermined degree (Hb'), that is, the flexible device 100 is bent such that the maximum height (Hb) from the horizontal surface to the flexible device 100 is a specific value (Hb') will be described with reference to FIG. 15.

Figure 15:
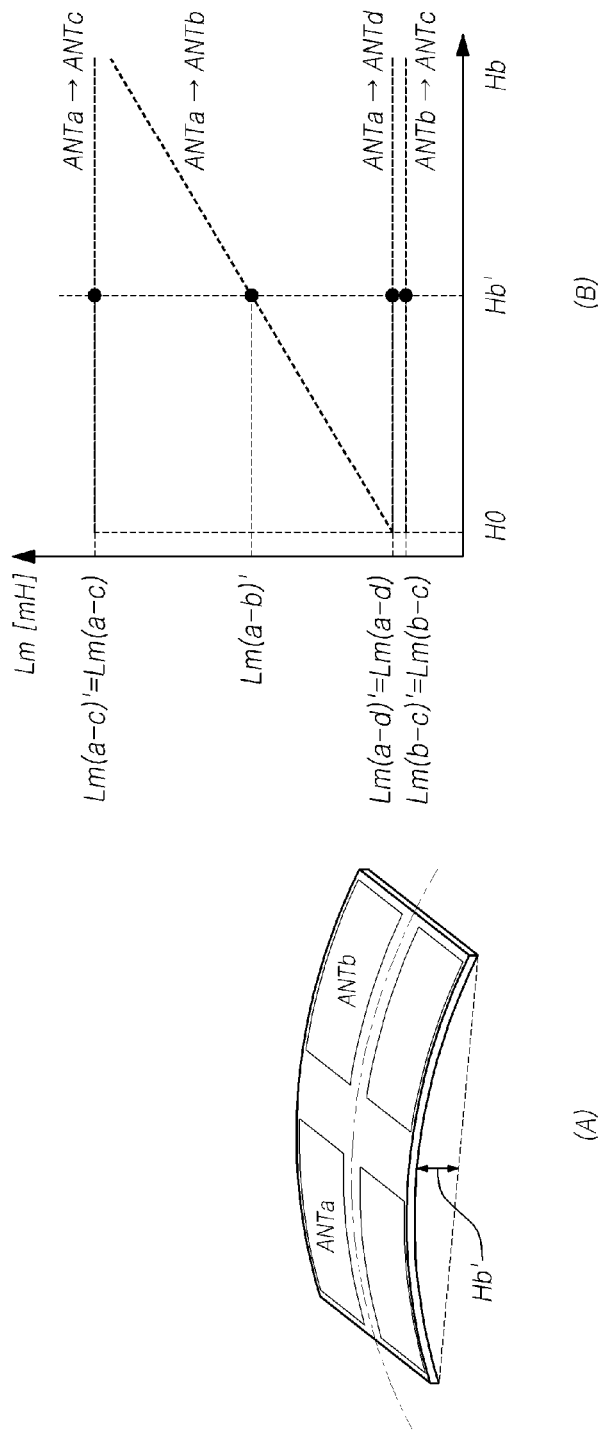
FIG. 15 is a view exemplifying that the bending (a first bending type) of the flexible device according to the present invention is detected based on mutual inductance.

FIG. 15 is a view exemplifying that the bending (a first bending type) of the flexible device 100 according to the present invention is detected based on mutual inductance.

FIG. 15A is a view showing a state in which the flexible device 100 is bent such that the maximum height (Hb) from the horizontal surface to the flexible device 100 is Hb'.

FIG. 15B is a graph depicting mutual inductances measured in the four pairs of antennas ANTa-ANTb, ANTa-ANTd, ANTa-ANTc, and ANTb-ANTc before and after the flexible device 100 is bent such that the maximum height (Hb) from the horizontal surface to the flexible device 100 is Hb'.

With reference to FIG. 15B, after the flexible device 100 is bent such that the maximum height (Hb) from the horizontal surface to the flexible device 100 is Hb', the mutual inductances measured in the four pairs of antennas ANTa-ANTb, ANTa-ANTd, ANTa-ANTc, and ANTb-ANTc may vary according to a degree by which the bending direction of the flexible device 100 corresponds to the directions Dab, Dad, Dac, and Dbc between the first antennas and the second antennas of the four pairs of antennas ANTa-ANTb, ANTa-ANTd, ANTa-ANTc, and ANTb-ANTc.

With reference to FIG. 15B, it can be seen that before and after the flexible device 100 is bent, of the change values of the mutual inductances measured in the four pairs of antennas ANTa-ANTb, ANTa-ANTd, ANTa-ANTc, and ANTb-ANTc, the change value of the mutual inductance measured in the pair of antennas ANTa-ANTb in which the first antenna and the second antenna are disposed in a direction the same as a transverse direction which is a bending direction of the flexible device 100.

That is, among a change value (ΔLm(a-b)=Lm(a-b)'−Lm(a-b)) of a mutual inductance measured in the pair of antennas ANTa-ANTb in which the first antenna and the second antenna are the antennas ANTa and ANTb before and after bending of the flexible device 100, a change value (ΔLm(a-d)=Lm(a-d)'−Lm(a-d)) of a mutual inductance measured in the pair of antennas ANTa-ANTd in which the first antenna and the second antenna are the antennas ANTa and ANTd before and after bending of the flexible device 100, a change value (ΔLm(a-c)=Lm(a-c)'−Lm(a-c)) of a mutual inductance measured in the pair of antennas ANTa-ANTc in which the first antenna and the second antenna are the antennas ANTa and ANTc before and after bending of the flexible device 100, and a change value (ΔLm(b-c)=Lm(b-c)'−Lm(b-c)) of a mutual inductance measured in the pair of antennas ANTb-ANTc in which the first antenna and the second antenna are the antennas ANTb and ANTc before and after bending of the flexible device 100, the change value (ΔLm(a-b) of the mutual inductance measured in the pair of antennas ANTa-ANTb disposed such that the first antenna and the second antenna ANTa and ANTb correspond to the bending direction (transverse direction) of the flexible device 100.

This is because after the flexible device 100 is bent, the mutual inductance (Lm(a-b)') measured in the pair of antennas ANTa-ANTb in which the first antenna and the second antenna are the antennas ANTa and ANTb increases most.

Thus, a transverse direction corresponding to a direction between the first antenna ANTa and the second antenna ANTb of the pair of antennas, of which the change value of the mutual inductance is largest before and after the flexible device 100 is bent, may be determined to be the bending direction of the flexible device 100.

Further, as an example, the bending detection unit 220 may determine a bending strength of the flexible device 100 to be Hb' or a value corresponding thereto by comparing the change values of the mutual inductances measured in the pairs of antennas before and after the flexible device 100 is bent with the change values (dotted lines of FIG. 15B) of the self-inductances according to bending strengths (1/Hb) for the pairs of antennas corresponding to reference information stored in advance.

With reference to FIG. 15, when the flexible device 100 is bent longitudinally as in the above-described method, bending may be detected by determining a bending direction, a bending strength, and the like.

Hereinafter, as a second bending type, mutual inductances (Lm) measured in the four pairs of antennas ANTa-ANTb, ANTa-ANTd, ANTa-ANTc, and ANTb-ANTc while a degree (bending strength) by which the flexible device 100 is bent diagonally is changed and change values thereof will be described with reference to FIG. 16, and an example of detecting bending of the flexible device 100 when the flexible device 100 is bent diagonally by a specific degree will be described with reference to FIG. 17.

Figure 16:
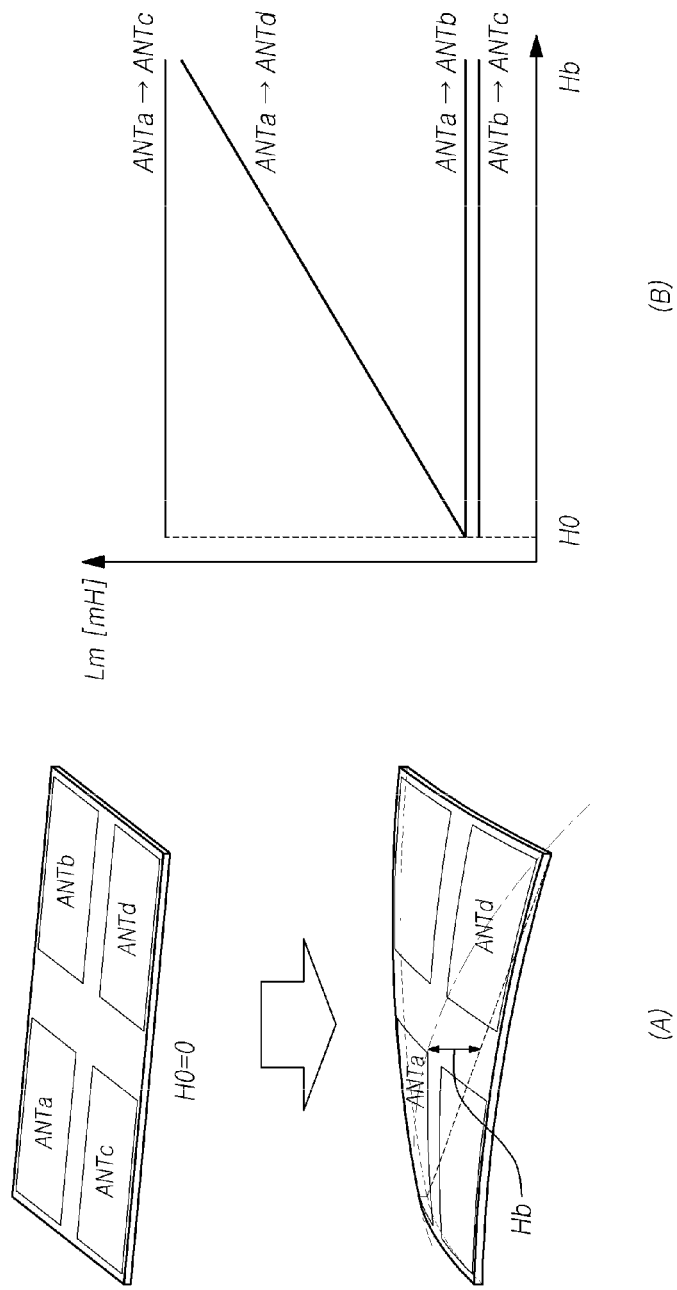
FIG. 16 is a view showing a change in a mutual inductance measured according to a second bending type when the bending of the flexible device according to an embodiment of the present invention is detected based on mutual inductances.

FIG. 16 is a view showing a change in a mutual inductance measured according to a second bending type (twisting) when the bending of the flexible device 100 according to an embodiment of the present invention is detected based on mutual inductances.

FIG. 16A is a view showing that a flat flexible device 100 is bent in a diagonal direction from an upper left end to a lower right end, and in a description related to detection of bending based on mutual inductance, a bending state is expressed by a maximum height Hb from the horizontal surface to the flexible device 100.

With reference to FIG. 16A, the height from the horizontal surface before the flexible device 100 is bent is H0=0 [mm], and as the flexible device 100 is bent in a diagonal direction from an upper left end to a lower right end, the maximum height Hb from the horizontal surface to the flexible device 100 becomes larger than H0 [mm].

That is, as the degree by which the flexible device 100 is bent in a diagonal direction from an upper left end to a lower right end becomes larger, the maximum height Hb [mm] from the horizontal surface to the flexible device 100 gradually becomes larger than H0 [mm].

In FIG. 16B, the x axis is a maximum height Hb from the horizontal surface to the flexible device 100, and represents a degree (bending strength) by which the flexible device 100 is bent diagonally. The y axis represents mutual inductances (Lm) measured in the four pairs of antennas ANTa-ANTb, ANTa-ANTd, ANTa-ANTc, and ANTb-ANTc formed by the four antennas ANTa to ANTd, and may be voltages (corresponding to the mutual inductances) measured in the pairs of antennas ANTa-ANTb, ANTa-ANTd, ANTa-ANTc, and ANTb-ANTc formed by the four antennas ANTa to ANTd.

With reference to FIG. 16B, as a degree by which the flexible device 100 is bent diagonally becomes higher, that is, a maximum height (Hb) from the horizontal surface to the flexible device 100 becomes larger, a degree by which the mutual inductance (Lm [mH]) is changed varies according to a degree by which the bending direction of the flexible device 100 corresponds to a direction Dab, Dad, Dac, and Dbc between the first antenna and the second antenna forming the pairs of antennas ANTa-ANTb, ANTa-ANTd, ANTa-ANTc, and ANTb-ANTc.

With reference to FIG. 16B, as a degree by which the flexible device 100 is bent diagonally becomes higher, that is, a maximum height (Hb) from the horizontal surface to the flexible device 100 becomes larger, the mutual inductance measured in the pairs of antennas ANTa-ANTd, of the considered four pairs of antennas ANTa-ANTb, ANTa-ANTd, ANTa-ANTc, and ANTb-ANTc in which the first antenna and the second antenna are disposed to most correspond to in a diagonal direction from an upper left end to a lower right end which is a bending direction of the flexible device 100 increases the most.

That is, the change value (ΔLm(a-d)=Lm(a-d)'−Lm(a-d)) of the mutual inductance measured in the pairs of antennas ANTa-ANTd in which the first antenna and the second antenna are the antennas ANTa and ANTd. Here, Lm(a-d) is a mutual inductance measured in the pair of antennas ANTa-ANTd in which the first antenna and the second antenna are the antennas ANTa and ANTd, and Lm(a-d)' is a mutual inductance measured in the pair of antennas ANTa-ANTd in which the first antenna and the second antenna are the antennas ANTa and ANTd after the flexible device 100 is bent and may be a value larger than Lm(a-d) before bending.

With reference to FIG. 16B, as the degree by which the flexible device 100 is bent diagonally becomes higher, that is, a maximum height (Hb) from the horizontal surface to the flexible device 100 becomes larger, the change of the mutual inductance measured in the pairs of antennas ANTa-ANTb, of the considered four pairs of antennas ANTa-ANTb, ANTa-ANTd, ANTa-ANTc, and ANTb-ANTc in which the first antenna and the second antenna are disposed to be farthest from corresponding to a bending direction of the flexible device 100 is a mere value.

Although the change values of the mutual inductances measured in the antennas ANTa-ANTb, ANTa-ANTc, and ANTb-ANTc may actually be small values, FIG. 16B conceptually shows that there is no change in the values for convenience of description.

Meanwhile, the bending detection apparatus 200 for the flexible device 100 may store the change values of the mutual inductances of the antennas according to a diagonal bending strength (Hb) as reference information.

Hereinafter, an example of detecting bending of the flexible device 100 when a flat flexible device 100 is bent by a predetermined degree (Hb'), that is, the flexible device 100 is bent such that the maximum height (Hb) from the horizontal surface to the flexible device 100 is a specific value (Hb') will be described with reference to FIG. 17.

Figure 17:
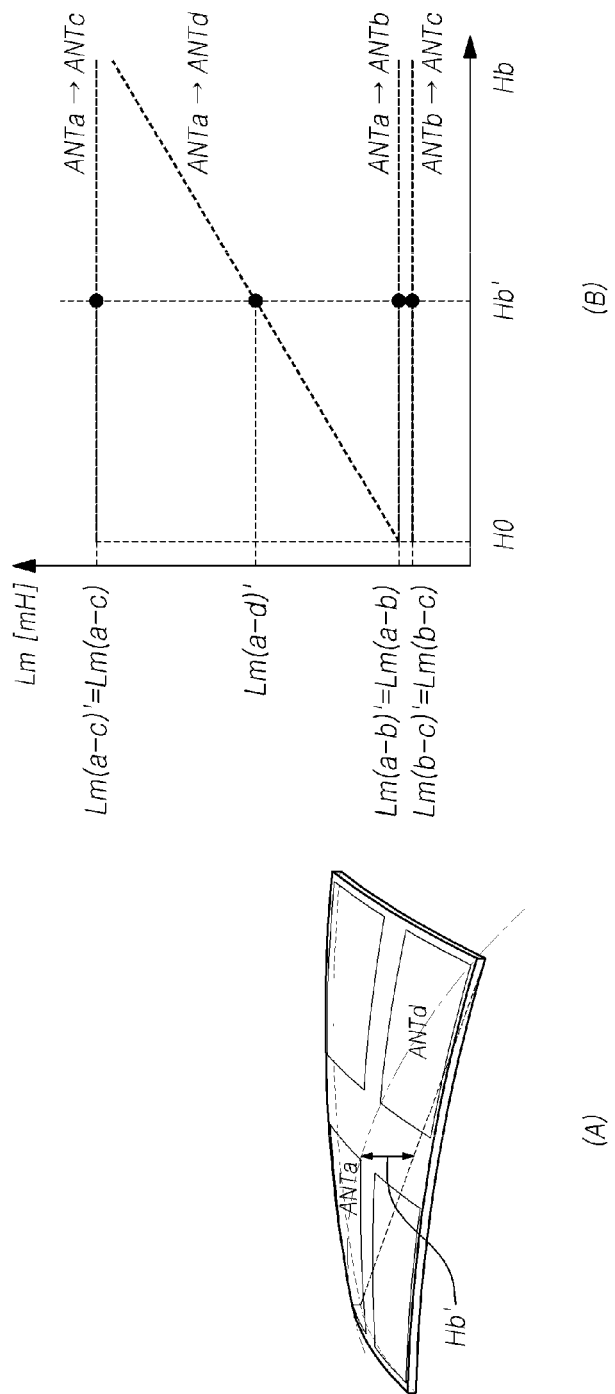
FIG. 17 is a view exemplifying that the bending (a second bending type) of the flexible device according to the present invention is detected based on mutual inductance.

FIG. 17 is a view exemplifying that the bending (a second bending type) of the flexible device 100 according to the present invention is detected based on a mutual inductance.

FIG. 17A is a view showing a state in which the flexible device 100 is bent such that the maximum height (Hb) from the horizontal surface to the flexible device 100 is Hb'.

FIG. 17B is a graph depicting mutual inductances measured in the four pairs of antennas ANTa-ANTb, ANTa-ANTd, ANTa-ANTc, and ANTb-ANTc before and after the flexible device 100 is bent such that the maximum height (Hb) from the horizontal surface to the flexible device 100 is Hb'.

With reference to FIG. 17B, after the flexible device 100 is bent such that the maximum height (Hb) from the horizontal surface to the flexible device 100 is Hb', the mutual inductances measured in the four pairs of antennas ANTa-ANTb, ANTa-ANTd, ANTa-ANTc, and ANTb-ANTc may vary according to a degree by which the bending direction of the flexible device 100 corresponds to the directions Dab, Dad, Dac, and Dbc between the first antennas and the second antennas of the four pairs of antennas ANTa-ANTb, ANTa-ANTd, ANTa-ANTc, and ANTb-ANTc.

With reference to FIG. 17B, it can be seen that before and after the flexible device 100 is bent, of the change values of the mutual inductances measured in the four pairs of inductances ANTa-ANTb, ANTa-ANTd, ANTa-ANTc, and ANTb-ANTc, the change value of the mutual inductance measured in the pair of antennas ANTa-ANTd in which the first antenna and the second antenna are disposed in a direction the same as a diagonal direction from an upper left end to a lower right end which is a bending direction of the flexible device 100 is maximal.

That is, among a change value ($\Delta Lm(a\text{-}b)=Lm(a\text{-}b)'-Lm(a\text{-}b)$) of a mutual inductance measured in the pair of antennas ANTa-ANTb in which the first antenna and the second antenna are the antennas ANTa and ANTb before and after bending of the flexible device 100, a change value ($\Delta Lm(a\text{-}d)=Lm(a\text{-}d)'-Lm(a\text{-}d)$) of a mutual inductance measured in the pair of antennas ANTa-ANTd in which the first antenna and the second antenna are the antennas ANTa and ANTd before and after bending of the flexible device 100, a change value ($\Delta Lm(a\text{-}c)=Lm(a\text{-}c)'-Lm(a\text{-}c)$) of a mutual inductance measured in the pair of antennas ANTa-ANTc in which the first antenna and the second antenna are the antennas ANTa and ANTc before and after bending of the flexible device 100, and a change value ($\Delta Lm(b\text{-}c)=Lm(b\text{-}c)'-Lm(b\text{-}c)$) of a mutual inductance measured in the pair of antennas ANTb-ANTc in which the first antenna and the second antenna are the antennas ANTb and ANTc before and after bending of the flexible device 100, the change value ($\Delta Lm(a\text{-}d)$) of the mutual inductance measured in the pair of antennas ANTa-ANTd disposed such that the first antenna and the second antenna ANTa and ANTd correspond to the bending direction (transverse direction) of the flexible device 100.

This is because after the flexible device 100 is bent, the mutual inductance ($Lm(a\text{-}d)'$) measured in the pair of antennas ANTa-ANTd in which the first antenna and the second antenna are the antennas ANTa and ANTd increases most.

Thus, a transverse direction corresponding to a direction between the first antenna ANTa and the second antenna ANTd of the pair of antennas of which the change value of the mutual inductance is largest before and after the flexible device 100 is bent, that is, a diagonal direction from an upper left end to a lower right end may be determined as a bending direction of the flexible device 100.

Further, as an example, the bending detection unit 220 may determine a bending strength of the flexible device 100 to be Hb' or a value corresponding thereto by comparing the change values of the mutual inductances measured in the pairs of antennas before and after the flexible device 100 is bent with the change values (dotted lines of FIG. 17B) of the self-inductances according to bending strengths (1/Hb) for the pairs of antennas corresponding to reference information stored in advance.

With reference to FIG. 17, when the flexible device 100 is bent in another diagonal direction (that is, a diagonal direction from an upper right end to a lower left end) as in the above-described method, bending may be detected by determining a bending direction, a bending strength, and the like.

Hereinafter, the bending detection method for a flexible device 100 which has been described with reference to FIGS. 1 to 17 will be briefly described again with reference to FIG. 18.

Figure 18:
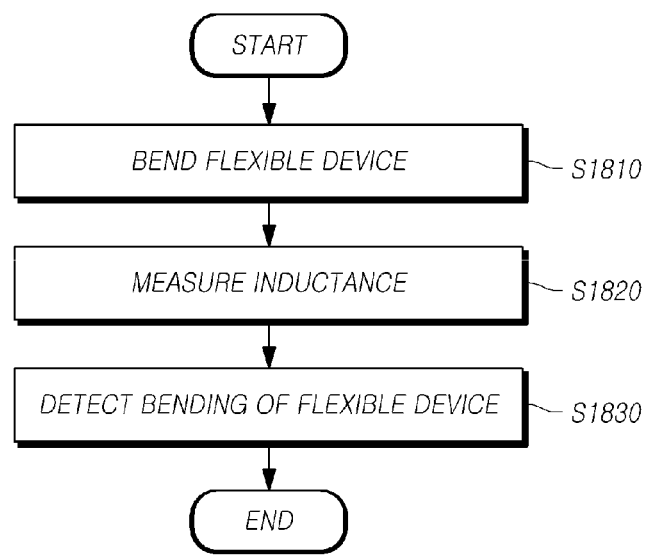
FIG. 18 is a flowchart of the bending detection method of a flexible device according to the embodiment of the present invention.

FIG. 18 is a flowchart of the bending detection method of a flexible device 100 according to the embodiment of the present invention.

With reference to FIG. 18, the bending detection method for a flexible device 100 according to the embodiment of the present invention includes bending the flexible device 100 (S1810), measuring inductances of a plurality of antennas disposed to be bent together with the flexible device 100 (S1820), and detecting bending of the flexible device 100 based on the measurement result for the inductances of the plurality of antennas (S1830).

As described above, the present invention provides a flexible device 100, and a method and an apparatus for detecting bending thereof. Meanwhile, although it is described in the specification that the bending detection unit 200 is a configuration included in the flexible device 100, the description is only an example for the convenience of description, and the bending detection unit 200 may be a configuration included in the flexible device 100 but may be the flexible device itself.

It will be apparent to those skilled in the art that various modifications and variations can be made in the present invention without departing from the spirit or scope of the invention. Thus, it is intended that the present invention cover the modifications and variations of this invention provided they come within the scope of the claims.

What is claimed is:

1. A bending detection apparatus for a flexible device, comprising:
a plurality of antennas disposed to be bent together with the flexible device; and
a bending detection circuit for detecting bending of the flexible device based on inductances of the plurality of antennas or information corresponding to the inductances,
wherein the bending detection circuit is configured to detect bending of the flexible device based on self-inductance of each of the plurality of antennas, or to detect bending of the flexible device based on mutual inductances of two or more pairs of antennas including a combination of a first antenna and a second antenna selected from the plurality of antennas.

2. The bending detection apparatus of claim 1, wherein the plurality of antennas are disposed at different locations, and
wherein the plurality of antennas are each elongated with respective elongation directions thereof at different angles with respect to a center of the flexible device, or the plurality of antennas are disposed to be symmetrical to each other with respect to a vertical line or a horizontal line.

3. The bending detection apparatus of claim 2, wherein the plurality of antennas comprise four or more antennas whose respective elongation directions are different from each other with at least one loop antenna disposed in a transverse direction of the flexible device, at least one loop antenna disposed in a longitudinal direction of the flexible device, and at least two loop antennas disposed in respective diagonal directions of the flexible device, and wherein the bending detection circuit detects a bending of the flexible device.

4. The bending detection apparatus of claim 1, wherein the bending detection circuit is configured to detect bending of the flexible device based on the self-inductance of each of the plurality of antennas, the plurality of antennas are each elongated with respective elongation directions that are different from each other.

5. The bending detection apparatus of claim 4, wherein the plurality of antennas are disposed such that opposite ends of at least one of the plurality of antennas become closer to each other than opposite ends of the remaining antennas whose disposition directions are different from that of the at least one of the plurality of antennas after the bending of the flexible device.

6. The bending detection apparatus of claim 4, wherein the plurality of antennas comprise three or more antennas whose respective elongation directions are different from each other with at least one loop antenna disposed in a transverse direction of the flexible device, at least one loop antenna disposed in a longitudinal direction of the flexible device, and at least one loop antenna disposed in a diagonal direction of the flexible device.

7. The bending detection apparatus of claim 4, wherein the bending detection circuit is configured to detect change values of self-inductances of the plurality of antennas before and after the flexible device is bent, to compare the detected change values of self-inductances of the plurality of antennas, and to determine a bending direction of the flexible device based on the comparison result and the elongation directions of the plurality of antennas.

8. The bending detection apparatus of claim 7, wherein the bending detection circuit determines a bending strength of the flexible device based on magnitudes of the detected change values of self-inductances of the plurality of antennas.

9. The bending detection apparatus of claim 7, wherein an antenna among the plurality of antennas disposed in a direction most closely corresponding to the bending direction of the flexible device has a largest change value in self-inductance among the plurality of antennas before and after the flexible device is bent.

10. The bending detection apparatus of claim 9, wherein, the antennas disposed in a direction corresponding to the bending direction of the flexible device have decreased self-inductances after the flexible device is bent.

11. The bending detection apparatus of claim 1, wherein when the bending detection circuit is configured to detect bending of the flexible device based on the mutual inductances of the two or more pairs of antennas, the plurality of antennas comprise three or more antennas disposed at different areas from each other such that each of the two or more pairs of antennas is formed by a combination of two respective antennas selected from the plurality of antennas.

12. The bending detection apparatus of claim 11, wherein directions between the two respective antennas forming each of the two or more pairs of antennas are different from each other.

13. The bending detection apparatus of claim 11, wherein the plurality of antennas are disposed in areas divided by at least one vertical line or at least one horizontal line of the flexible device.

14. The bending detection apparatus of claim 13, wherein positions of the antennas are symmetrical to each other with respect to the at least one vertical line or the at least one horizontal line.

15. The bending detection apparatus of claim 11, wherein the plurality of antennas are disposed such that, after the flexible device is bent, a change in a distance between at least one antenna pair of the two or more pairs of antennas is greater than a change in a distance between the remaining antenna pairs of the two or more pairs of antennas.

16. The bending detection apparatus of claim 11, wherein the bending detection circuit is configured to detect change values of mutual inductances of the two or more pairs of antennas before and after the flexible device is bent, to compare the detected change values of mutual inductances of the two or more pairs of antennas, and to determine a bending direction of the flexible device based on the comparison result and directions between the two respective antennas forming each of the two or more pairs of antennas.

17. The bending detection apparatus of claim 16, wherein the bending detection circuit determines a bending strength of the flexible device based on magnitudes of the detected change values of mutual inductances of the plurality of antennas.

18. The bending detection apparatus of claim 16, wherein a pair of antennas of the two or more pairs of antennas having a direction therebetween most closely corresponding to the bending direction of the flexible device has a largest change value in self-inductance before and after the flexible device is bent among the pairs of antennas.

19. The bending detection apparatus of claim 18, wherein a pair of antennas disposed such that a direction therebetween corresponds to the bending direction of the flexible device has the greatest increase in mutual inductance among the pairs of antennas as the flexible device is bent.

20. The bending detection apparatus of claim 1, wherein the plurality of antennas are each elongated with respective elongation directions thereof that are different from each other, and wherein the plurality of antennas overlap at a center of the flexible device.

21. The bending detection apparatus of claim 1, wherein the plurality of antennas are separate loops.

\* \* \* \* \*